US008118811B2

(12) United States Patent
Coon et al.

(10) Patent No.: US 8,118,811 B2
(45) Date of Patent: Feb. 21, 2012

(54) APPARATUS FOR KNEE SURGERY AND METHOD OF USE

(75) Inventors: Thomas M. Coon, Redding, CA (US);
E. Marlowe Goble, Alta, WY (US);
Alfred J. Tria, Jr., Princeton, NJ (US);
Warren Scott Gareiss, Columbia City, IN (US); Robert A. Hodorek, Wasaw, IN (US); Toby N. Farling, Warsaw, IN (US); Daniel F. Justin, Logan, UT (US); Donald M. Smucker, Perrysburg, OH (US); Richard R. Van Zile, Bryan, OH (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 12/638,590

(22) Filed: Dec. 15, 2009

(65) Prior Publication Data

US 2010/0094300 A1      Apr. 15, 2010

Related U.S. Application Data

(60) Division of application No. 12/191,835, filed on Aug. 14, 2008, now abandoned, which is a continuation of application No. 10/357,282, filed on Feb. 3, 2003, now abandoned.

(51) Int. Cl.
*A61B 17/58* (2006.01)
*A61B 17/60* (2006.01)
*A61F 2/00* (2006.01)

(52) U.S. Cl. ............................ 606/88; 606/86 R; 606/87
(58) Field of Classification Search ................ 606/86 R, 606/87, 88
See application file for complete search history.

(56) References Cited

U.S. PATENT DOCUMENTS

| 1,170,334 A | 2/1916 | Riggs |
| 2,564,118 A | 8/1951 | Mahorner |
| 4,457,307 A | 7/1984 | Stillwell |
| 4,487,203 A | 12/1984 | Androphy |
| 4,524,766 A | 6/1985 | Petersen |
| 4,565,192 A | 1/1986 | Shapiro |
| 4,566,448 A | 1/1986 | Rohr, Jr. |

(Continued)

FOREIGN PATENT DOCUMENTS
EP          0538152 B1       8/1995
(Continued)

OTHER PUBLICATIONS

NexGen Complete Knee Solution—The Zimmer Institute Surgical Technique MIS Quad-Sparing Surgical Technique for Total Knee Arthroplasty, 2004.

(Continued)

*Primary Examiner* — Thomas C. Barrett
*Assistant Examiner* — Christine Nelson
(74) *Attorney, Agent, or Firm* — Faegre Baker Daniels

(57) ABSTRACT

The present invention comprises a set of instruments and a method for their use in preparing a knee joint to receive knee implants. The inventive instruments and method are generally suitable for knee joint surgery. Furthermore, they include features that make them suitable for performing a minimally invasive knee surgery in which a smaller than normal incision is made and oriented to preserve the quadriceps mechanism and protect the suprapatellar pouch. The instruments permit switching from a minimally invasive technique to a standard open technique at any point in the procedure. An illustrative set of instruments for total knee arthroplasty and an associated minimally invasive technique are described.

18 Claims, 19 Drawing Sheets

U.S. PATENT DOCUMENTS

| | | | |
|---|---|---|---|
| 4,574,794 A | 3/1986 | Cooke |
| 4,633,862 A | 1/1987 | Peterson |
| 4,653,488 A | 3/1987 | Kenna |
| 4,718,413 A | 1/1988 | Johnson |
| 4,721,104 A | 1/1988 | Kaufman |
| 4,722,330 A | 2/1988 | Russell et al. |
| 4,736,737 A | 4/1988 | Fargie et al. |
| 4,759,350 A | 7/1988 | Dunn et al. |
| 4,841,975 A | 6/1989 | Woolson |
| 4,892,093 A | 1/1990 | Zarnowski et al. |
| 4,926,847 A | 5/1990 | Luckman |
| 4,926,849 A | 5/1990 | Downey |
| 4,935,023 A | 6/1990 | Whiteside et al. |
| 4,952,213 A | 8/1990 | Bowman et al. |
| 5,002,545 A | 3/1991 | Whiteside et al. |
| 5,002,547 A | 3/1991 | Poggie et al. |
| 5,007,912 A | 4/1991 | Albrektsson |
| 5,035,699 A | 7/1991 | Coates |
| 5,047,032 A | 9/1991 | Jellicoe |
| 5,053,039 A | 10/1991 | Hofmann et al. |
| 5,080,675 A | 1/1992 | Lawes et al. |
| 5,098,436 A | 3/1992 | Ferrante |
| 5,100,409 A | 3/1992 | Coates |
| 5,108,401 A | 4/1992 | Insall et al. |
| 5,122,144 A | 6/1992 | Bert et al. |
| 5,129,907 A | 7/1992 | Heldreth |
| 5,129,908 A | 7/1992 | Peterson |
| 5,176,684 A | 1/1993 | Ferrante |
| 5,180,384 A | 1/1993 | Mikhail |
| 5,207,680 A | 5/1993 | Dietz |
| 5,219,362 A | 6/1993 | Tuke et al. |
| 5,222,955 A | 6/1993 | Mikhail |
| 5,234,433 A | 8/1993 | Bert et al. |
| 5,275,603 A | 1/1994 | Ferrante et al. |
| 5,282,803 A | 2/1994 | Lackey |
| 5,284,482 A | 2/1994 | Mikhail |
| 5,306,285 A | 4/1994 | Miller et al. |
| 5,330,533 A | 7/1994 | Walker |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz |
| 5,364,401 A | 11/1994 | Ferrante et al. |
| 5,364,402 A | 11/1994 | Mumme et al. |
| 5,415,663 A | 5/1995 | Luckman et al. |
| 5,417,694 A | 5/1995 | Marik et al. |
| 5,417,695 A | 5/1995 | Axelson |
| 5,431,656 A | 7/1995 | Clift, Jr. et al. |
| 5,451,228 A | 9/1995 | Johnson et al. |
| 5,454,816 A | 10/1995 | Ashby |
| 5,474,559 A | 12/1995 | bertin |
| 5,484,446 A | 1/1996 | Burke et al. |
| 5,486,178 A | 1/1996 | Holdge |
| 5,486,180 A | 1/1996 | Dietz |
| 5,514,139 A | 5/1996 | Goldstein |
| 5,514,140 A | 5/1996 | Lackey |
| 5,520,692 A | 5/1996 | Ferrante |
| 5,520,695 A | 5/1996 | Luckman |
| 5,536,271 A | 7/1996 | Daly et al. |
| 5,540,696 A | 7/1996 | Booth |
| 5,569,261 A | 10/1996 | Marik et al. |
| 5,593,411 A | 1/1997 | Stalcup |
| 5,597,379 A | 1/1997 | Haines |
| 5,601,563 A | 2/1997 | Burke et al. |
| 5,609,639 A | 3/1997 | Walker |
| 5,611,802 A | 3/1997 | Samuelson et al. |
| 5,628,750 A * | 5/1997 | Whitlock et al. ............ 606/88 |
| 5,643,272 A | 7/1997 | Haines et al. |
| 5,649,928 A | 7/1997 | Grundei |
| 5,658,291 A | 8/1997 | Techiera |
| 5,658,292 A | 8/1997 | Axelson |
| 5,658,293 A | 8/1997 | Vanlaningham |
| 5,662,656 A | 9/1997 | White |
| 5,667,512 A | 9/1997 | Johnson |
| 5,669,914 A | 9/1997 | Eckhoff |
| 5,676,668 A | 10/1997 | McCue et al. |
| 5,681,316 A | 10/1997 | DeOrio et al. |
| 5,683,397 A | 11/1997 | Vendrely et al. |
| 5,688,280 A | 11/1997 | Booth |
| 5,688,281 A | 11/1997 | Cripe et al. |
| 5,693,048 A | 12/1997 | Stalcup |
| 5,702,466 A | 12/1997 | Pappas et al. |
| 5,716,360 A | 2/1998 | Baldwin et al. |
| 5,716,362 A | 2/1998 | Treacy |
| 5,720,752 A | 2/1998 | Elliott et al. |
| 5,743,915 A | 4/1998 | Bertin |
| 5,749,876 A | 5/1998 | Duvillier et al. |
| 5,755,803 A | 5/1998 | Haines |
| 5,769,855 A | 6/1998 | Bertin |
| 5,782,920 A | 7/1998 | Colleran |
| 5,788,700 A | 8/1998 | Morawa et al. |
| 5,810,827 A | 9/1998 | Haines |
| 5,810,831 A | 9/1998 | D'Antonio |
| 5,830,216 A | 11/1998 | Insall |
| 5,853,415 A | 12/1998 | Bertin |
| 5,860,981 A | 1/1999 | Bertin |
| 5,879,354 A | 3/1999 | Haines |
| 5,885,298 A | 3/1999 | Herrington et al. |
| 5,908,424 A | 6/1999 | Bertin |
| 5,910,143 A | 6/1999 | Cripe et al. |
| 5,911,723 A | 6/1999 | Ashby et al. |
| 5,914,884 A | 6/1999 | Gur et al. |
| 5,916,219 A | 6/1999 | Matsuno et al. |
| 6,010,509 A | 1/2000 | Delgado et al. |
| 6,013,081 A | 1/2000 | Burkinshaw et al. |
| 6,056,754 A | 5/2000 | Haines |
| 6,059,831 A | 5/2000 | Braslow et al. |
| 6,077,270 A | 6/2000 | Katz |
| 6,090,114 A | 7/2000 | Matsuno et al. |
| 6,096,043 A | 8/2000 | Techiera et al. |
| 6,102,954 A | 8/2000 | Albrektsson et al. |
| 6,159,246 A | 12/2000 | Mendes et al. |
| 6,174,314 B1 | 1/2001 | Waddell |
| 6,197,064 B1 | 3/2001 | Haines |
| 6,267,762 B1 | 7/2001 | Millard et al. |
| 6,551,325 B2 | 4/2003 | Neubauer et al. |
| 6,554,837 B1 | 4/2003 | Hauri et al. |
| 6,575,980 B1 | 6/2003 | Robie et al. |
| 6,595,997 B2 | 7/2003 | Axelson, Jr. et al. |
| 6,685,711 B2 | 2/2004 | Axelson, Jr. et al. |
| 6,695,848 B2 | 2/2004 | Haines |
| 6,712,824 B2 | 3/2004 | Millard et al. |
| 6,740,092 B2 | 5/2004 | Lombardo et al. |
| 6,770,077 B2 | 8/2004 | Van Zile et al. |
| 6,932,823 B2 | 8/2005 | Grimm et al. |
| 6,942,700 B2 | 9/2005 | Williamson |
| 7,048,741 B2 | 5/2006 | Swanson |
| 7,101,401 B2 | 9/2006 | Brack |
| 7,309,339 B2 | 12/2007 | Cusick et al. |
| 7,344,540 B2 | 3/2008 | Smucker et al. |
| 2002/0133160 A1 | 9/2002 | Axelson, Jr. et al. |
| 2002/0133162 A1 | 9/2002 | Axelson, Jr. et al. |
| 2003/0069585 A1 | 4/2003 | Axelson, Jr. et al. |
| 2003/0069591 A1 | 4/2003 | Carson et al. |
| 2003/0100907 A1 | 5/2003 | Rosa et al. |
| 2003/0171757 A1 | 9/2003 | Coon et al. |
| 2003/0212403 A1 | 11/2003 | Swanson |
| 2004/0039396 A1 | 2/2004 | Couture et al. |
| 2004/0122305 A1 | 6/2004 | Grimm et al. |
| 2004/0153066 A1 | 8/2004 | Coon et al. |
| 2004/0153083 A1 | 8/2004 | Nemec et al. |
| 2004/0162561 A1 | 8/2004 | Marchyn et al. |
| 2005/0021039 A1 | 1/2005 | Cusick et al. |
| 2005/0049603 A1 | 3/2005 | Calton et al. |
| 2005/0070910 A1 | 3/2005 | Keene |
| 2005/0149039 A1 | 7/2005 | Haines et al. |
| 2005/0149041 A1 | 7/2005 | McGinley et al. |
| 2005/0171545 A1 | 8/2005 | Walsh et al. |
| 2005/0182415 A1 | 8/2005 | Steffensmeier et al. |
| 2005/0187557 A1 | 8/2005 | Collazo |
| 2005/0203528 A1 | 9/2005 | Couture et al. |
| 2005/0234466 A1 | 10/2005 | Stallings |
| 2006/0149276 A1 | 7/2006 | Grimm |
| 2006/0200158 A1 | 9/2006 | Farling et al. |
| 2007/0186738 A1 | 8/2007 | McGinley et al. |
| 2007/0219559 A1 | 9/2007 | Heavener et al. |

| | | |
|---|---|---|
| 2007/0233138 A1 | 10/2007 | Figueroa et al. |
| 2008/0114366 A1 | 5/2008 | Smucker et al. |
| 2008/0306484 A1 | 12/2008 | Coon et al. |

FOREIGN PATENT DOCUMENTS

| | | |
|---|---|---|
| EP | 0556998 B1 | 6/1997 |
| EP | 0720834 B1 | 6/1999 |
| EP | 0839501 B1 | 3/2003 |
| EP | 1323386 A2 | 7/2003 |
| EP | 1430842 A1 | 6/2004 |
| EP | 1442712 A1 | 8/2004 |
| EP | 1574177 A1 | 9/2005 |
| EP | 1579812 A1 | 9/2005 |
| EP | 1424042 B1 | 3/2007 |
| JP | 08-098842 A | 4/1996 |
| WO | WO96/07361 A1 | 3/1996 |
| WO | WO96/29940 A1 | 10/1996 |

OTHER PUBLICATIONS

Zimmer, Inc. Nexgen Complete Knee Solution, Intramedullary Instrumentation Surgical Technique for the NexGen Cruciate Retaining & Legacy Posterior Stabilized knee, 97-5973-102 Rev. 1, 1995, 1997, 1998.

Zimmer, Inc. Nexgen Complete Knee Solution, Multi-Reference 4-in-1 Femoral Instrumentation, Posterior Reference Surgical Technique, 97-5973-402 Rev. 1, 1998, 2000.

Zimmer, Inc. Nexgen Complete Knee Solution, Revision Instrumentation Surgical Technique for Legacy Knee Constrained Condylar Knee, 97-35994-202, 2001.

Zimmer, Inc. Nexgen Complete Knee Solution, Extramedullary/Intramedullary Tibial Resector Surgical Technique, 97-5997-02 Rev. 1, 2000, 2002.

Zimmer, Inc. Nexgen Complete Knee Solution, Primary/Revision Surgical Technique for NexGen Rotating Hinge Knee (RHK), 97-5880-02, 2002.

Zimmer, Inc. Nexgen Complete Knee Solution, Surgical Technique for the Legacy Knee LPS-Flex Fixed Bearing Knee, 97-5964-02 Rev. 1, 2000, 2002.

Zimmer, Inc. Nexgen Complete Knee Solution, Surgical Technique for the Legacy Posterior Stabilized Knees, 97-5996-02, 2002.

Zimmer, Inc. MIS Minimally Invasive Solution, The MIG Unicompartmental Knee Minimally Invasive Surgical Technique, 97-5791-02, 2002Aug. 14, 2008.

Zimmer, Inc. Nexgen Complete Knee Solution, Surgical Technique for Cruciate Retaining Knees and Revision Instrumentation Surgical Technique for Cruciate Retaining Augmentable Knees, 97-5970-202, 2002.

Zimmer, Inc. Revision Knee Arthroplasty Surgical Guidelines, 2nd Edition, 97-5224-03, 1999.

* cited by examiner

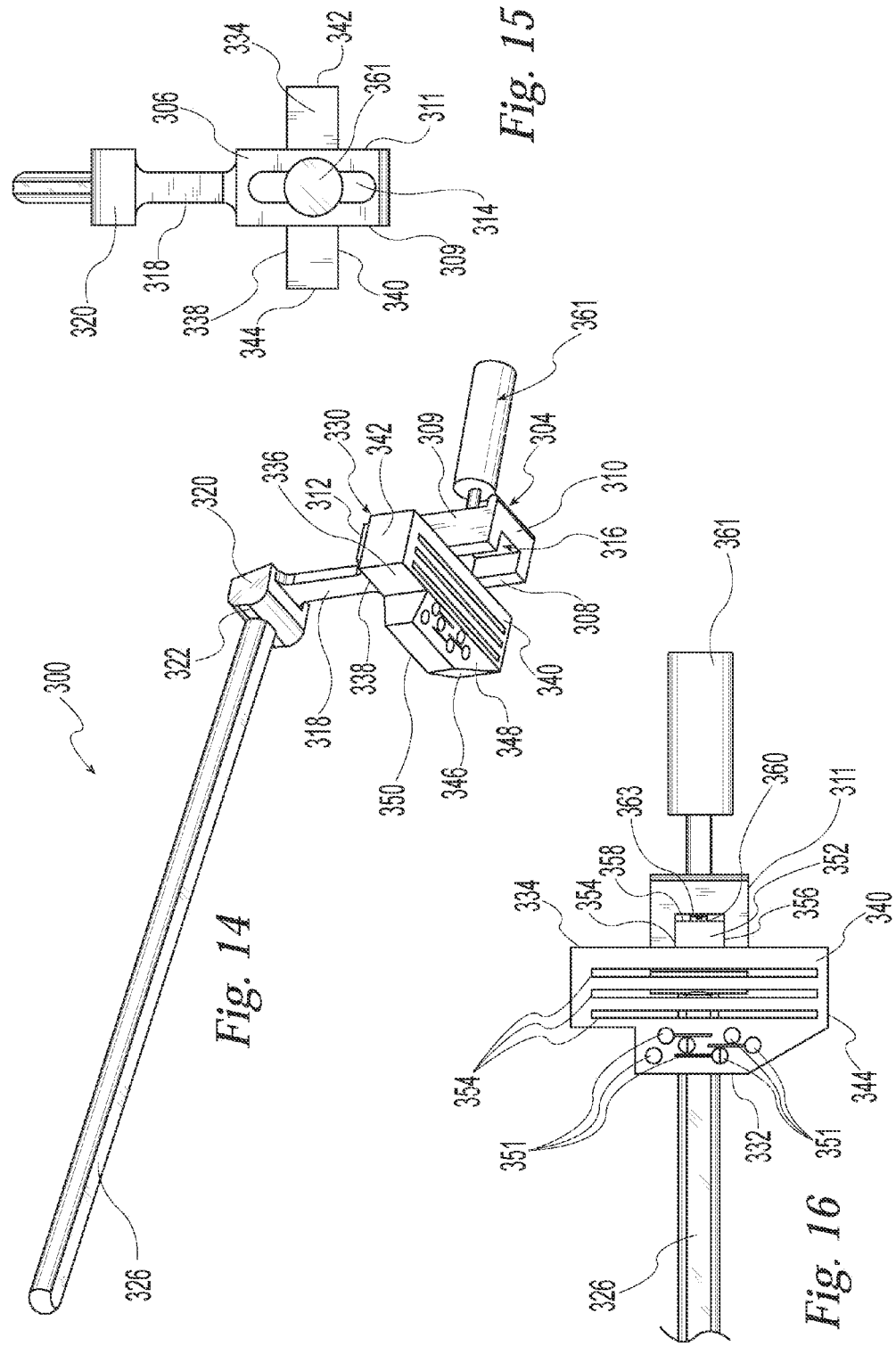

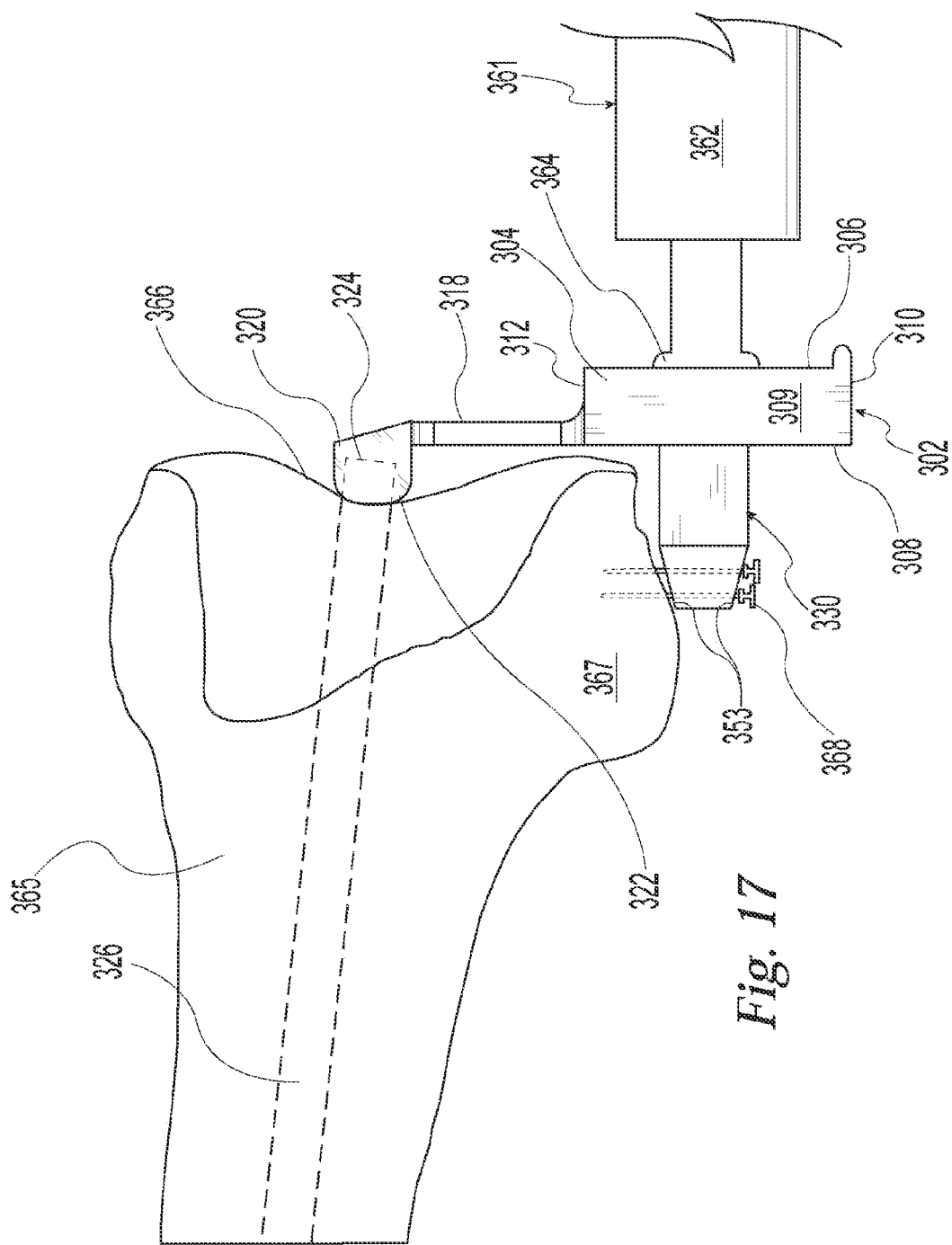

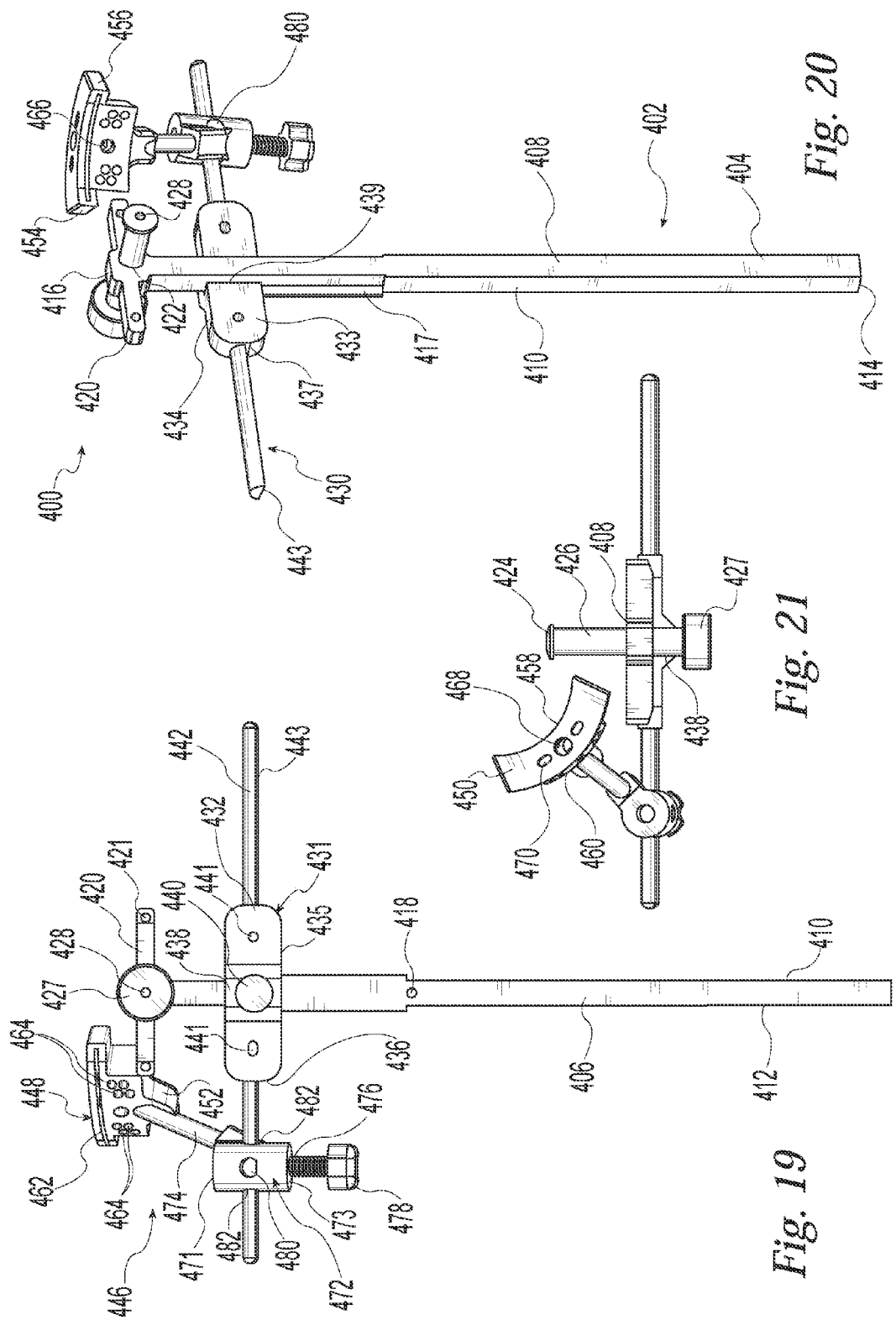

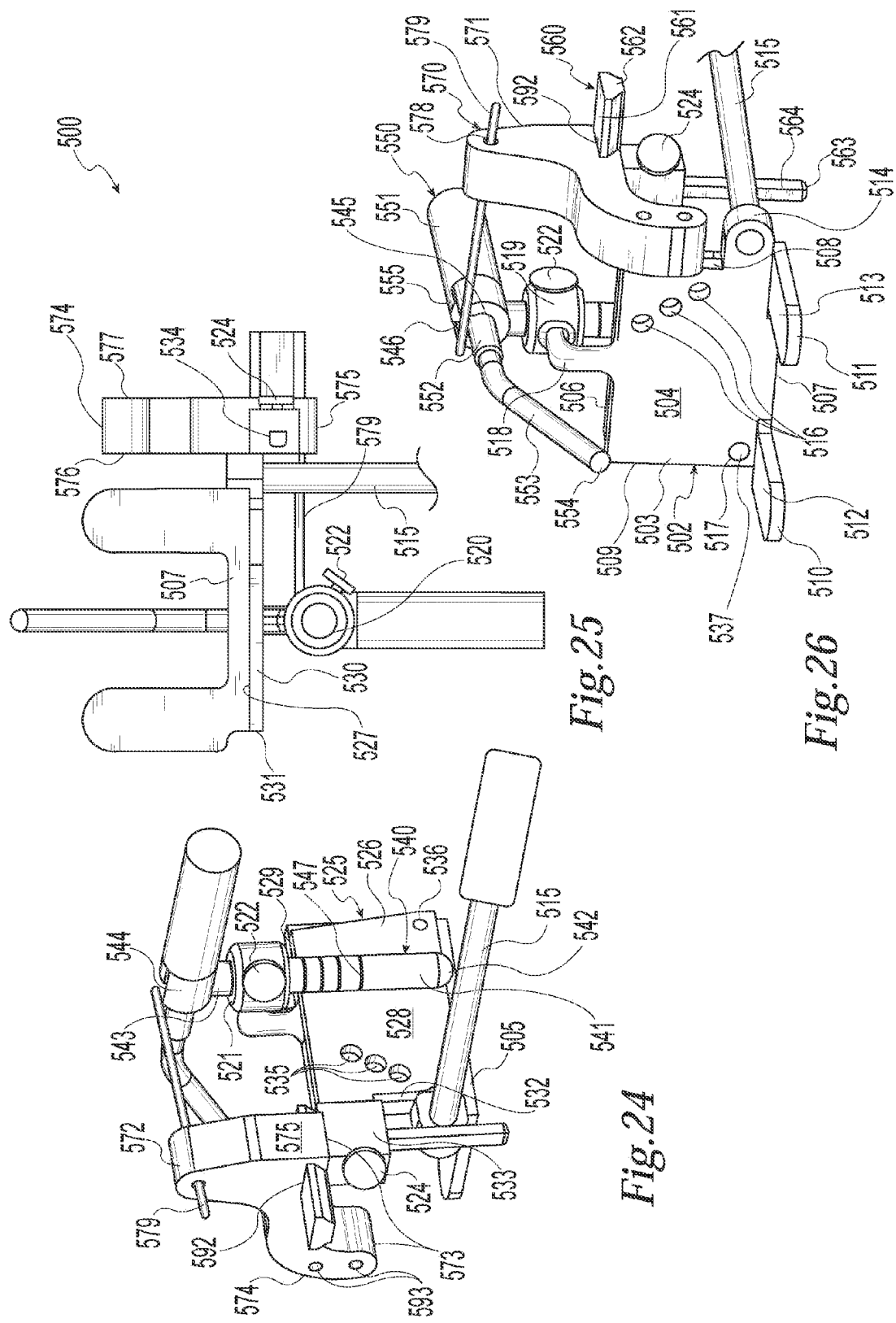

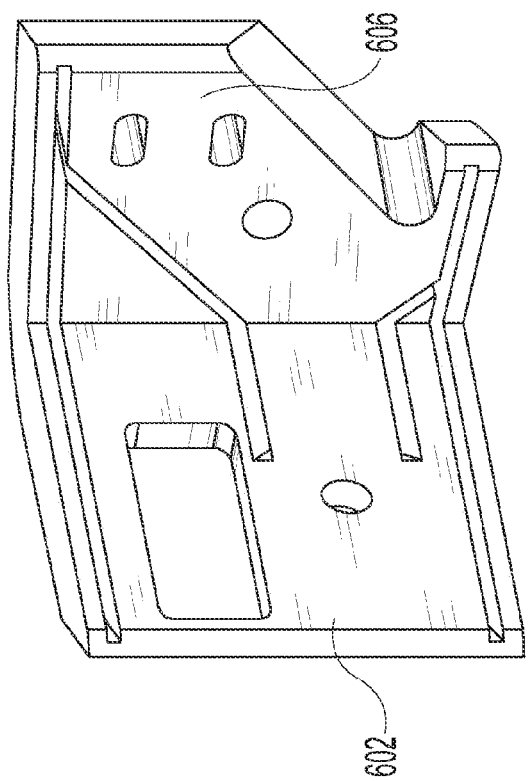
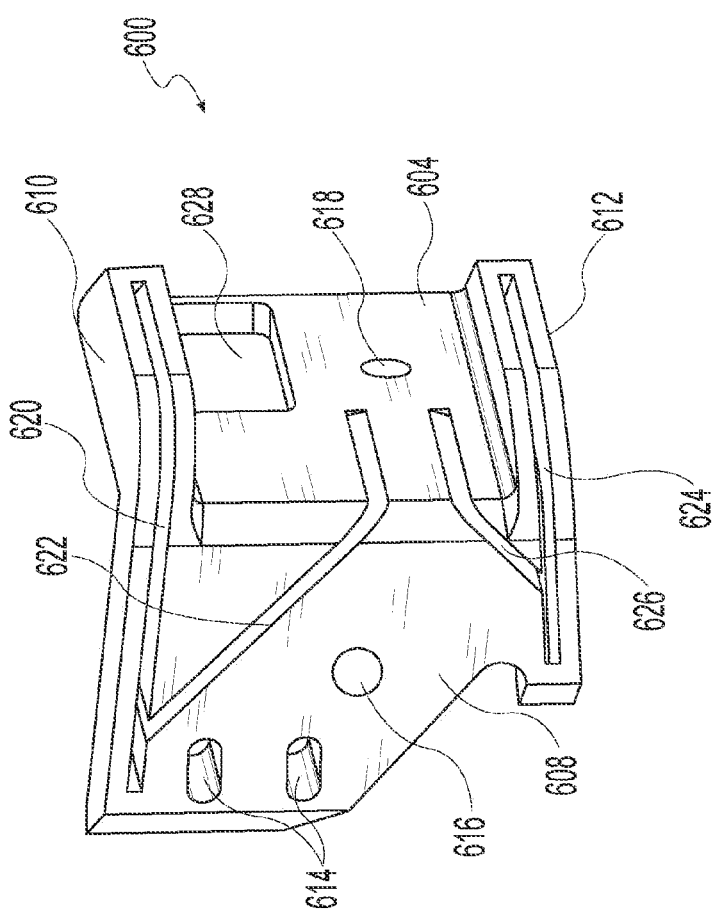

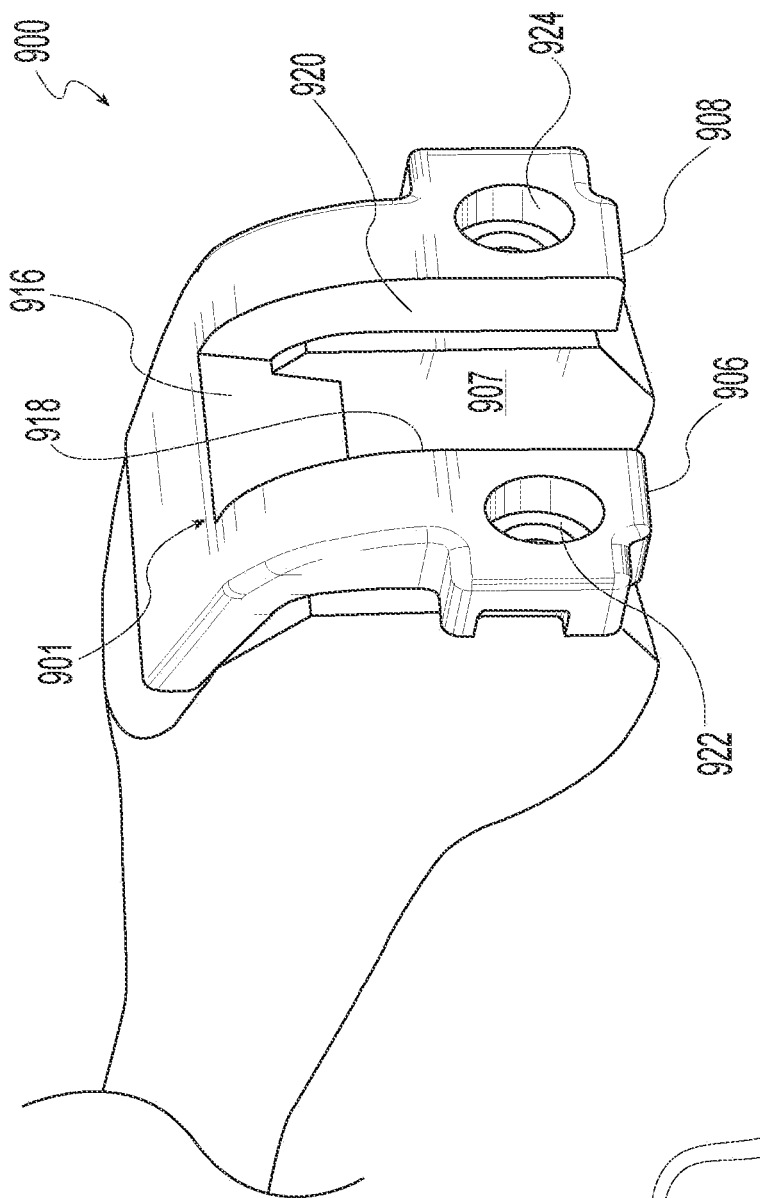
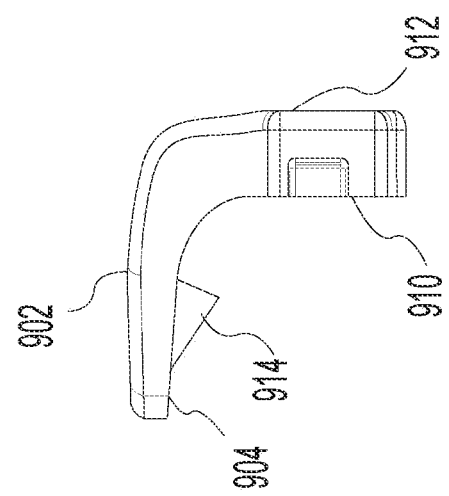
Fig. 36
Fig. 35

US 8,118,811 B2

APPARATUS FOR KNEE SURGERY AND METHOD OF USE

CROSS-REFERENCE TO RELATED APPLICATIONS

This application is a Divisional of U.S. patent application Ser. No. 12/191,835 filed Aug. 14, 2008, which is a Continuation of U.S. patent application Ser. No. 10/357,282 filed Feb. 3, 2003, the disclosures of which are hereby expressly incorporated by reference herein.

FIELD OF THE INVENTION

The present invention relates to methods and instruments for performing total knee arthroplasty.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 14 is a perspective view of an illustrative embodiment of an intramedullary distal femoral cutting instrument according to the present invention.

FIG. 15 is a side elevation view of the intramedullary distal femoral cutting instrument of FIG. 14.

FIG. 16 is a front elevation view of the intramedullary distal femoral cutting instrument of FIG. 14.

FIG. 17 is a side elevation view of the intramedullary distal femoral cutting instrument of FIG. 14 mounted on a femur.

FIG. 19 is a front elevation view of an illustrative embodiment of a tibial cut guide assembly according to the present invention.

FIG. 20 is a perspective view of the tibial cut guide assembly of FIG. 19.

FIG. 21 is a top plan view of the tibial cut guide assembly of FIG. 19.

FIG. 24 is a perspective view of an illustrative embodiment of a femoral A/P sizer and pin guide assembly according to the present invention.

FIG. 25 is a bottom plan view of the femoral A/P sizer and pin guide assembly of FIG. 24.

FIG. 26 is a perspective view, from a different viewing angle, of the femoral A/P sizer and pin guide assembly of FIG. 24.

FIG. 30 is a perspective view of an illustrative embodiment of a femoral profile cut block according to the present invention.

FIG. 31 is a perspective view, from a different viewing angle, of the femoral profile cut block of FIG. 30.

FIG. 35 is a side elevation view of the intercondylar notch guide of FIG. 39.

FIG. 36 is a perspective view of an illustrative embodiment of an intercondylar notch guide mounted on a femur according to the present invention.

DESCRIPTION OF THE ILLUSTRATED EMBODIMENTS

The present invention relates to methods and instruments for performing total knee arthroplasty. An incision is made into the knee joint to expose the bones comprising the joint. Cutting guides are then used to guide the removal of the articular surfaces that are to be replaced. Artificial joint components are then positioned to replace the resected bone ends in order to establish the desired alignment and mechanics of the joint. Each aspect of the surgery affects the ultimate outcome of the procedure. The incision location and size determines the extent to which the bones can be exposed for facilitating the bone cutting steps. The incision also affects the amount of trauma to the soft tissues surrounding the joint and therefore the pain, time for recovery, and stability of the joint postoperatively. The design of the cutting guides affects how much exposure is required to place and orient the guides relative to the bones. The precision of the cuts produced by the guides affects the stability and longevity of the joint replacement. Finally, the manner in which the joint components attach to one another and to the bone affects the amount of exposure required and the stability and longevity of the joint replacement. The inventive instruments and method are generally suitable for knee joint surgery. Furthermore, they include features that make them suitable for performing a minimally invasive knee surgery in which a smaller than normal incision is made and oriented to preserve the quadriceps mechanism and protect the suprapatellar pouch. The instruments permit switching from a minimally invasive technique to a standard open technique at any point in the procedure.

Figure 1:
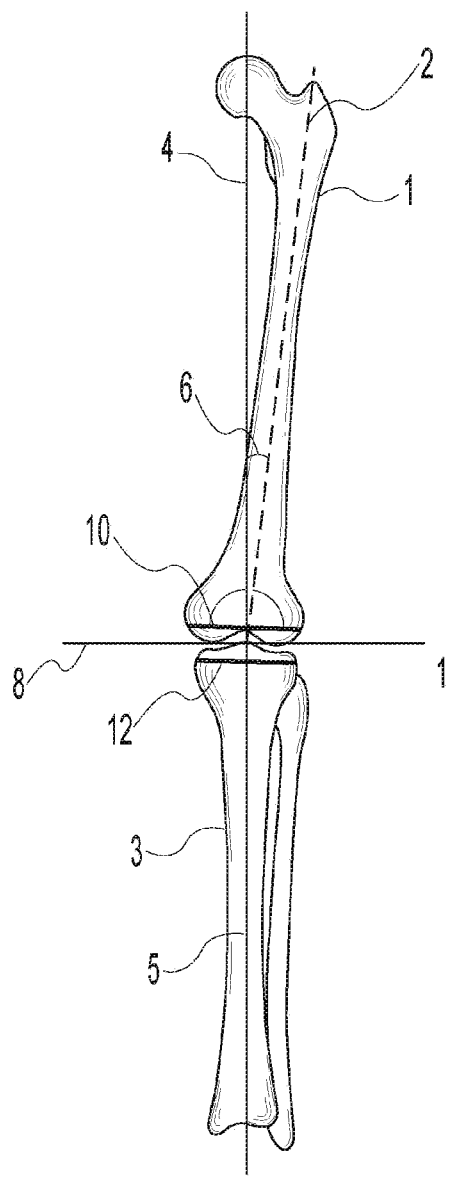
FIG. 1 is a front elevation view of a tibia and a femur showing axes of the knee joint.
Figure 2:
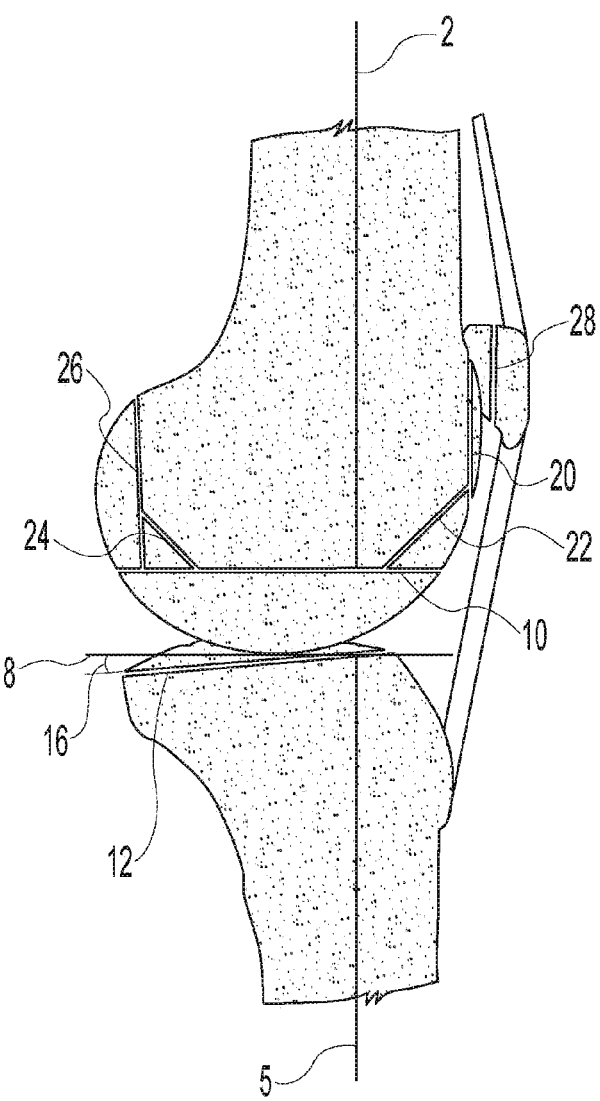
FIG. 2 is a side section view of a knee joint showing typical bone cuts used in replacing the joint surfaces.
Figure 3:
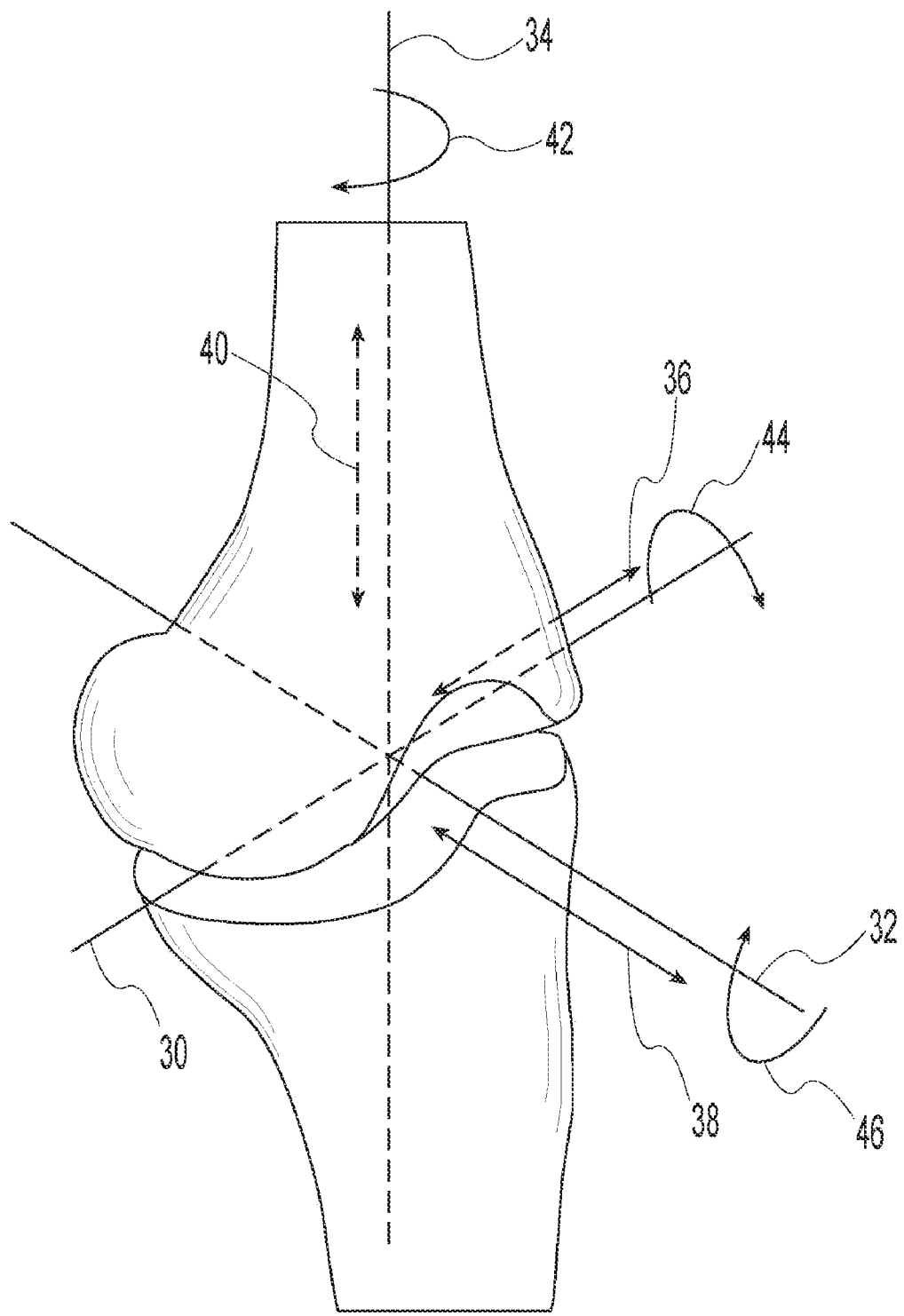
FIG. 3 is a perspective view of knee joint showing aspects of component positioning.

In order to better understand the total knee arthroplasty procedure, it is helpful to understand the relationship of the bones and the cuts made to orient the implant components. FIGS. 1-3 illustrate several aspects of implant orientation. FIG. 1 illustrates various axes of the lower limb in the frontal plane. Axes can be defined for each segment of the lower limb. For example, the femur 1 has an anatomic axis 2 coinciding generally with its intramedullary canal. It also has a mechanical axis 4, or load axis, running from the center of the femoral head to the center of the knee. The angle 6 between these two axes varies within the patient population but is on the order of 6°. Likewise, the tibia 3 has an anatomic axis coinciding generally with its intramedullary canal. The mechanical axis 5 of the tibia runs from the center of the knee to the center of the ankle and is generally collinear with the anatomic axis. The transverse axis, or joint line 8, about which the knee flexes, is parallel to a line through the medial and lateral femoral condyles and parallel to the tibial plateau. This line subtends a slight valgus angle of approximately 87° with the mechanical axis of the femur and a slight varus angle of approximately 87° with the mechanical axis of the tibia. Thus, the distal femur is in slight valgus and the proximal tibia is in slight varus. Normally, the distal femur and proximal tibia are resected to be parallel to the joint line 8, and thus perpendicular to the mechanical axis 4, as indicated at 10 and 12. The intersection of the femoral and tibial mechanical axes, 4 and 5, may subtend a small angle relative to one another. However, the angle is small and the mechanical axis of the femur has an approximately normal alignment with the proximal tibia if the knee is uninjured. Therefore the tibial mechanical axis may be extrapolated to the distal femur to define the femoral mechanical axis in the distal femur when there is a femoral deformity. Similarly, if there is a deformity in the tibia, the mechanical axis of the proximal tibia may be defined by extrapolating the femoral mechanical axis. The illustrative procedure described herein restores the center of the femoral head, the knee, and the ankle to a lie on a straight line to establish a neutral mechanical axis. The femoral and tibial components are oriented perpendicular to this axis in the frontal plane.

FIG. 2 illustrates the knee joint from the side or sagittal view and various bone cuts that may be made to align implant components. The distal femur is typically cut 10 perpendicular, in the anterior-to-posterior direction, to the anatomic axis 2 of the femur. The proximal tibial resection 12 is normally cut to match the natural posterior slope of the proximal tibia relative to the tibial mechanical axis 5. The amount of posterior slope 16 relative to a reference line 18 perpendicular to the tibial mechanical axis 5 varies in the patient population but is on the order of 7°. The distance between the distal femoral 10 and proximal tibial 12 cuts along the mechanical axes 4 and 5 is the extension gap. Other cuts may be made depending on the components that are to be implanted. These include an anterior femoral cut 20, anterior femoral chamfer cut 22, posterior femoral chamfer cut 24, and posterior femoral cut 26. The patella 7 may also be cut 28 to allow for replacement of the patellar articular surface. Additional preparation of the bone may include drilling or notching the bones to receive pegs, stems, and other extensions from the components (not shown).

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Position along the x, y, and z axes determines the medial/lateral (dx) 36, anterior/posterior (dy) 38, and proximal/distal (dz) 40 positioning of components respectively. Rotation about each of these axes is also depicted by arrows. Rotation about the z-axis (rz) 42 corresponds anatomically to external rotation of the femoral component, while rotation about the x-axis (rx) 44 and y-axis (ry) 46, corresponds to extension plane slope and varus/valgus angle respectively. Depending on the order of the cuts, and the way that subsequent instruments reference each cut, the position of the distal femoral cut 10 can affect the location of the joint line (dz), the extension gap, the varus/valgus angle (ry), and the extension plane angle (rx). Likewise, the position of the proximal tibial cut 12 can affect the varus/valgus angle (ry), extension plane (rx), external rotation (rz), and the joint line (dz) or extension gap. The position of the anterior 20, posterior 26, and chamfer 22 and 24 femoral cuts affect anterior/posterior size and placement (dy) and external rotation (rz). Finally, the position of peg holes, stem notches, and other similar bone cuts affect medial/lateral (dx) placement of components.

Figure 4:
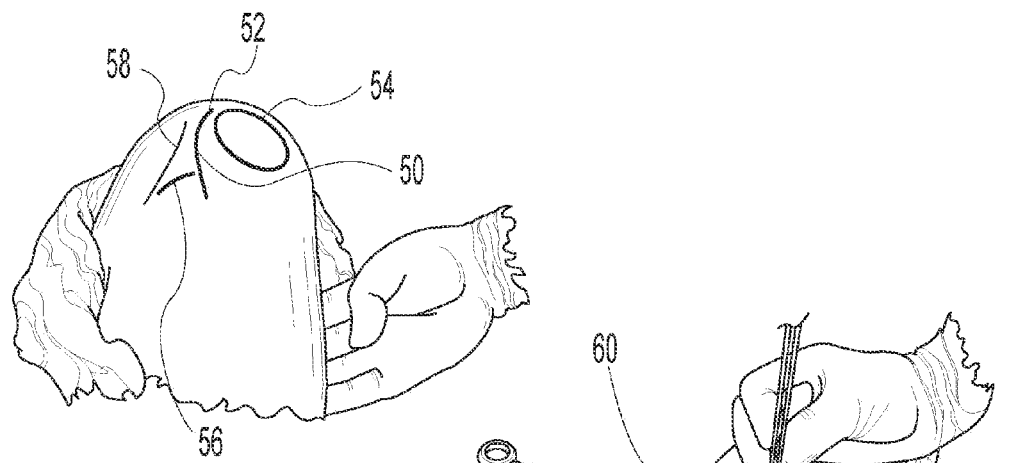
FIG. 4 is a perspective view of the knee joint showing the incision planning for a medial surgical approach according to the present invention.
Figure 5:
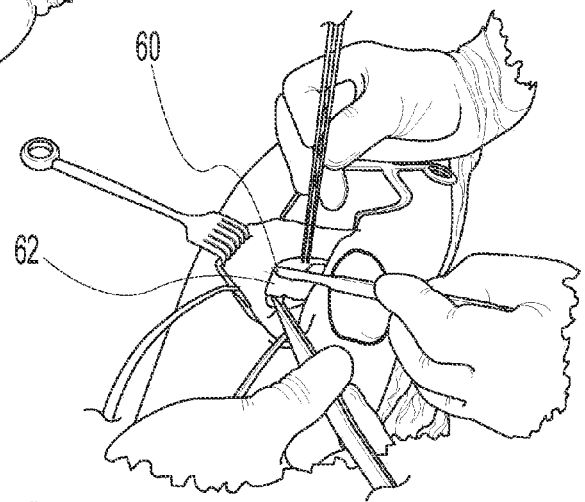
FIG. 5 is a perspective view of the knee joint showing the medial incision according to the present invention.
Figure 6:
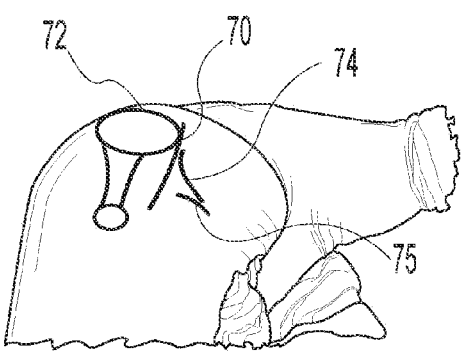
FIG. 6 is a perspective view of the knee joint showing the incision planning for a lateral surgical approach according to the present invention.
Figure 7:
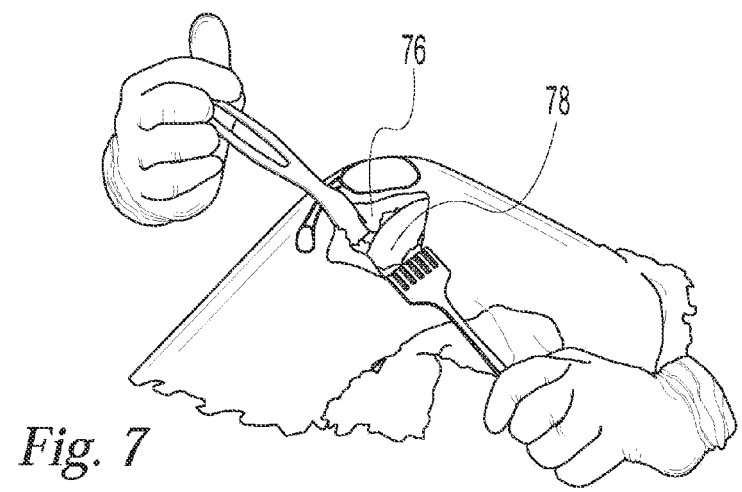
FIG. 7 is a perspective view of the knee joint showing the lateral incision according to the present invention.

An illustrative set of instruments for total knee arthroplasty and an associated minimally invasive technique will now be described with reference to the drawings. The illustrative technique utilizes a limited exposure approach from the side of the knee as shown in FIGS. 4-7. This side approach can be at an oblique angle relative to the front of the knee or transversely, more directly from the side. The side approach permits a minimally invasive knee surgery in which a smaller than normal incision is made and orients the incision and subsequent bone cuts to preserve the quadriceps mechanism and protect the suprapatellar pouch. FIGS. 4 and 5 depict a medial approach and FIGS. 6 and 7 depict a lateral approach. Reference lines are made on the knee prior to making the incision. For the medial approach, a curvilinear medial incision 50 is made from the superior pole 52 of the patella 54 to the tibial joint line 56. The outline of the medial femoral condyle 58 is also marked. The arthrotomy is in line with the skin incision and includes a transverse incision 60 beneath the vastus medialis to increase the exposure of the medial femoral condyle 62. Alternatively, a lateral approach may be used. For the lateral approach, the incision 70 is made on the lateral side of the patella 72 to the tibial joint line 74 and is almost vertical along the side of the patella. The outline of the lateral femoral condyle 75 is also marked. The arthrotomy is performed in a vertical fashion and the iliotibial band 76 is peeled from the tibial plateau joint line from anterior to posterior to expose the lateral femoral condyle 78. No transverse capsular incision is used for the lateral approach.

Throughout the description of the illustrative technique and instruments, reference will be made to cutting bone. There are many cutters for surgically cutting bone including: oscillating saws, reciprocating saws, gigli saws, end cutting reamers, side cutting reamers, streams of particles, energy beams, and others known in the art. While the illustrative embodiments depict and describe saw blade guides for guiding a saw blade to cut bone, any means for cutting bone is contemplated. The slots can be replaced with surfaces, jigs, clamps, and other types of fixtures as appropriate to guide the type of cutter being used.

The preparation of the patella is described first. However, the patella can be prepared later if desired. Preparing it first results in more space anteriorly when preparing the distal femur. The illustrative instruments allow preparation of the patella without everting it to avoid damage to the patellar mechanism. Alternatively, waiting until after the distal femur and/or proximal tibia are prepared allows the joint to be collapsed to reduce tension in the patellar tendon and ligament and improve access to prepare the patella.

Figure 8:
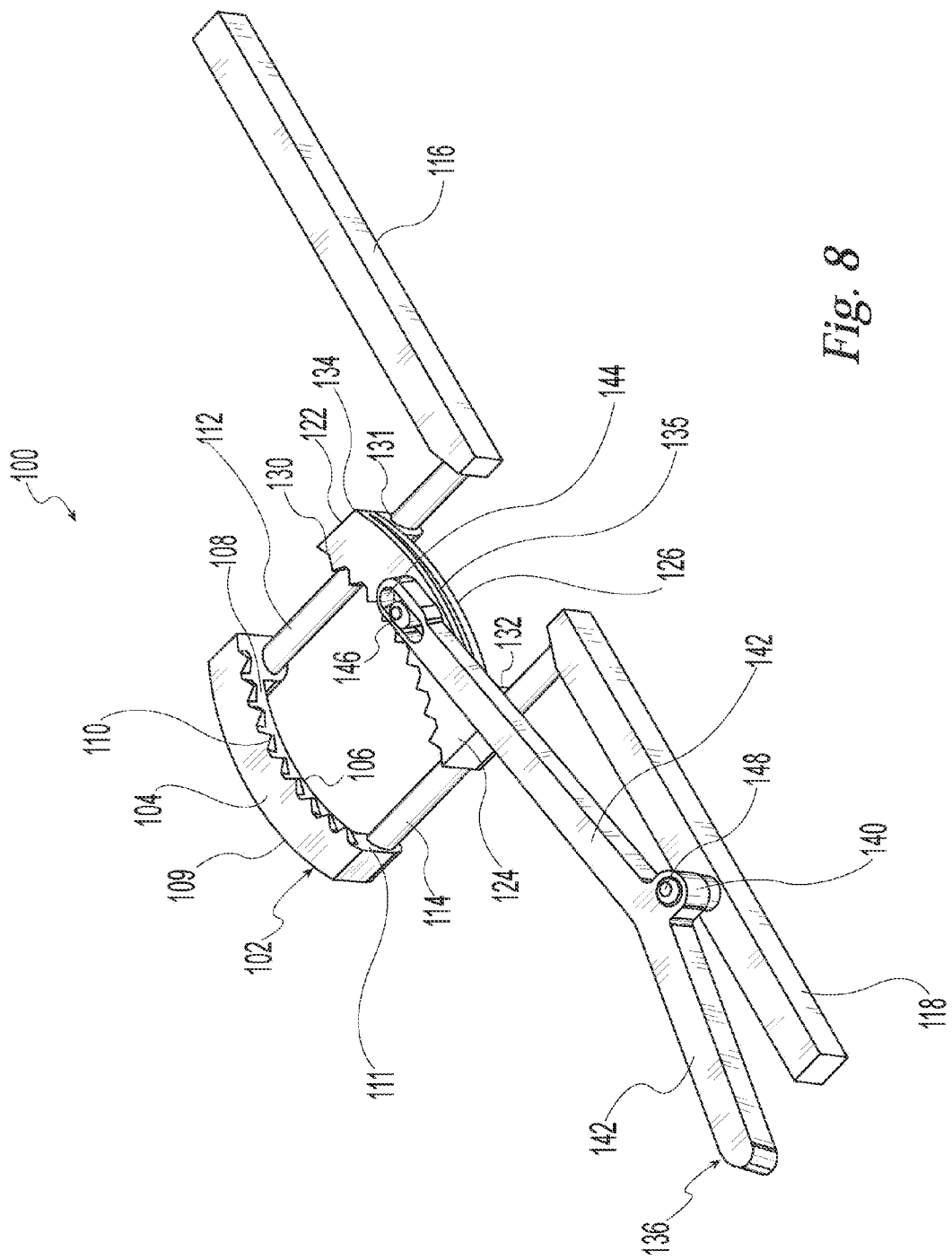
FIG. 8 is a perspective view of an illustrative embodiment of a patella resection guide according to the present invention.
Figure 9:
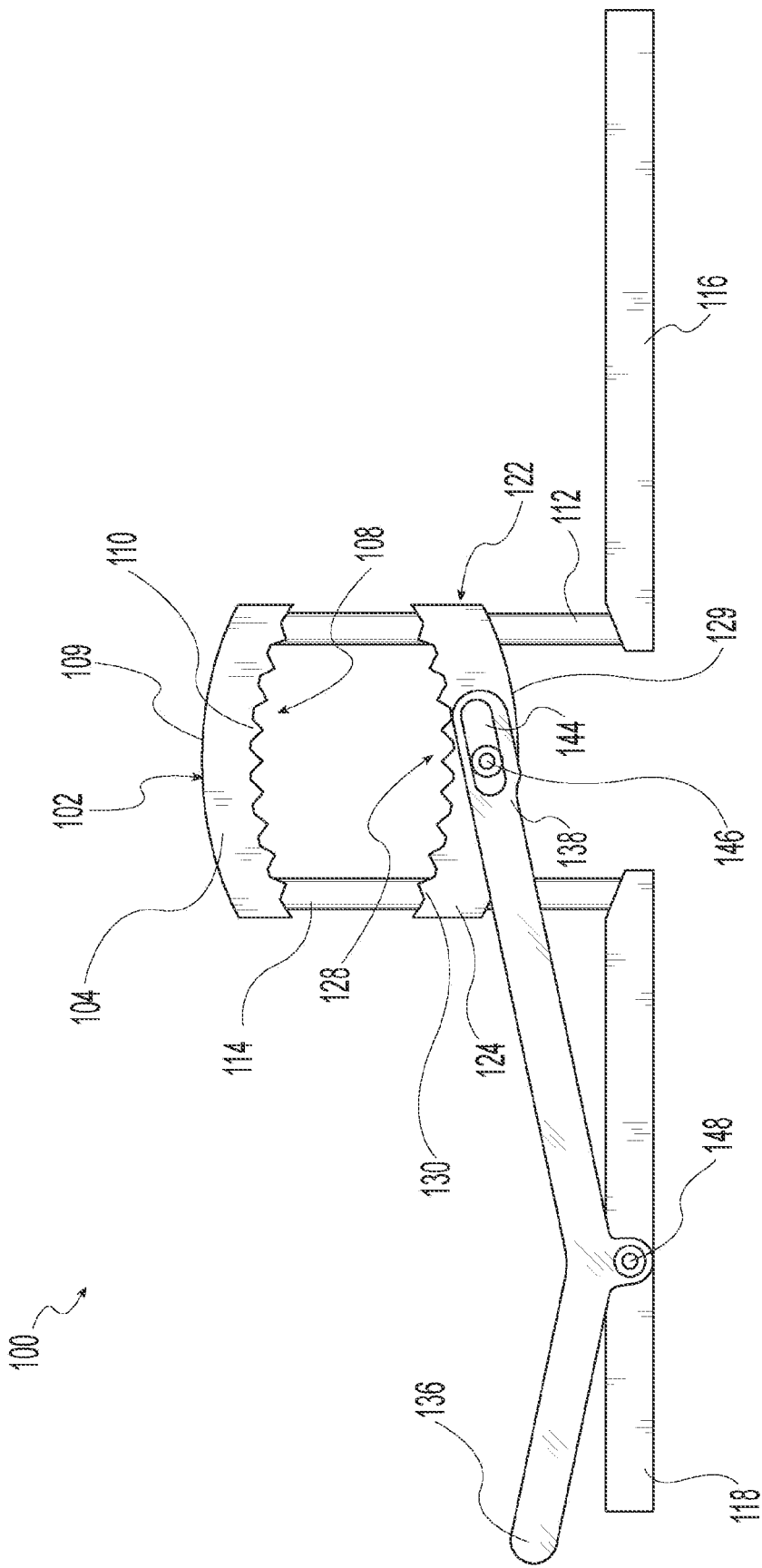
FIG. 9 is a top plan view of the patella resection guide of FIG. 8.
Figure 10:
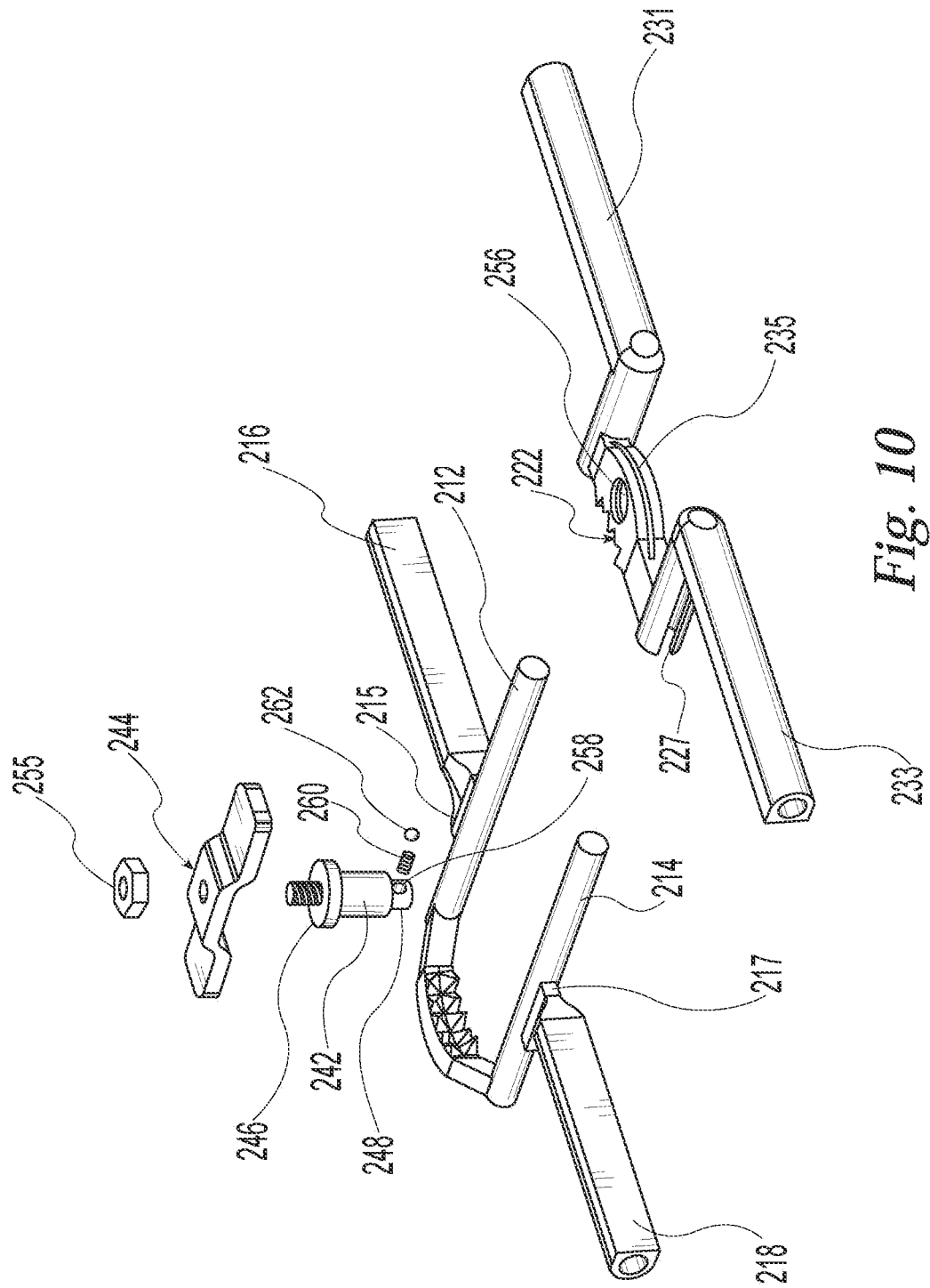
FIG. 10 is an exploded perspective view of another illustrative embodiment of a patella resection guide according to the present invention.

The patella is prepared using a patella resection guide. FIGS. 8 and 9 illustrate one embodiment of a patella resection guide 100. Stationary jaw member 102 includes a top surface 104, a bottom surface 106, an inner concave surface 108, an opposite outer surface 109, and teeth 110 projecting inwardly from the concave surface 108, adjacent the top surface 104. Guide arms 112, 114 project from the concave surface 108 and connect the concave surface to a pair of handles 116, 118. The guide arms 112, 114 are generally perpendicular to the jaw member 102 and parallel to one another. The pair of handles 116, 118 are coplanar and are attached generally perpendicularly to the guide arms 112, 114 and extend in opposite directions from one another. A top portion 111 of the stationary jaw 102, including the teeth 110 and top surface 104, projects above the guide arms 112, 114. Translating jaw member 122 includes a top surface 124, a bottom surface 126, an inner concave surface 128, an opposite outer surface 129, and teeth 130 projecting inwardly from the concave surface 128, adjacent the top surface 124. Bores 131, 132 through the translating jaw member 122 provide bearing surfaces in engagement with guide arms 112, 114 such that the translating jaw member 122 may be moved along the guide arms 112, 114 in a motion plane from a first position in which the two jaw members 102, 122 are spaced from one another and the translating jaw 122 is nearer the handles 116, 118 and a second position in which the two jaw members 102, 122 are closer to one another and the translating jaw 122 is farther from the handles 116, 118. This arrangement constrains the jaws to remain parallel to one another as they move relative to one another. A top portion 134, including the teeth 130 and top surface 124, of the translating jaw 122 projects above the guide arms 112, 114 such that the tops 104, 124 of the jaws 102, 122 are coplanar. The translating jaw 122 further includes a saw guide slot 135 extending through the top portion 134 from the outer surface 129 to the inner concave surface 128 parallel to the top surface 124 and extending beyond the attachment point of the guide arms to the handles on either side. The slot 135 is positioned so that it is above the level of the handles 116, 118 to permit easy access for the insertion of a saw blade anywhere across the entire width of the slot 135. The slot 135 defines a cutting plane parallel to the motion plane of the translating jaw 122. Actuator 136 comprises an elongate lever having a jaw engaging end 138, a pivot portion 140, and an input end 142. The jaw engaging end 138 further includes a slot 144 through which a pin 146 connects the jaw engaging end 138 to the translating jaw 122. The jaw engaging end 138 can pivot and translate via the slot 144 relative to the pin 146 which is fixed to the translating jaw 122. The actuator 136 is pivotally constrained by a pin 148 extending through the pivot portion 140 and being fixed to the handle 118. Input end 142 extends at an angle to the handle 118 when the jaws 102, 122 are in a first position in which they are spaced from one another. In use, a user grips the handles 116, 118 and squeezes the input end 142 of the actuator 136 to reduce the angle between the input end 142 and the handle 118. As the actuator pivot portion 140 rotates about its pin 148, the jaw engaging end 138 presses against its pin 146 and moves the translating jaw 122 toward the stationary jaw 102.

FIGS. 10-13 illustrate another embodiment of a patella resection guide 200. Stationary jaw member 202 includes a top surface 204, a bottom surface 206, a concave inner surface 208, an opposite convex outer surface 209, and teeth 210 projecting inwardly from the concave surface 208, adjacent the top surface 204. Guide arms 212, 214 project from the concave surface 208 and connect the concave surface to a pair of handles 216, 218 via rectangular bosses 215, 217. The guide arms 212, 214 are generally perpendicular to the jaw member 202 and parallel to one another. The handles 216, 218 are coplanar and are attached generally perpendicularly to the guide arms 212, 214 and extend in opposite directions from one another. In this embodiment, the guide arms 212, 214 extend past their connections 215, 217 to the handles 216, 218. A top portion 211, including the teeth 210 and top surface 204, of the stationary jaw 202 projects above the guide arms 212, 214. A translating jaw member 222 includes a top surface 224, a bottom surface 226, an inner concave surface 228, an opposite convex outer surface 229, and teeth 230 projecting inwardly from the concave surface 228, adjacent the top surface 224. Cannulated guide sleeves 221, 223 connect to opposite sides of the translating jaw 222 and connect the concave surface 228 to a pair of handles 231, 233. The guide sleeves 221, 223 are coplanar and are generally perpendicular to the translating jaw 222 and parallel to one another. The pair of handles 231, 233 are attached generally perpendicularly to the guide sleeves 221, 223 and extend oppositely and outwardly from the translating jaw 222. The guide sleeves 221, 223 have outwardly facing slots 225, 227 in their outer wall communicating with their inner cannulae. The guide sleeves 221, 223 receive guide arms 212, 214 such that the translating jaw member 222 may be moved along the guide arms 212, 214 from a first position in which the two jaw members 202, 222 are spaced from one another and the translating handles 231, 233 are spaced from the stationary handles 216, 218 and a second position in which the jaw members and handles are closer to one another. This arrangement constrains the jaw members to remain parallel and facing one another while they move relative to one another. A top portion 234, including the teeth 230 and top surface 224, of the translating jaw 222 projects above the guide sleeves 221, 223 such that the tops 204, 224 of the jaws 202, 222 are coplanar. The translating jaw 222 further includes a saw guide slot 235 extending through the top portion 234 from the outer surface 229 to the inner surface 228 parallel to the top surface 224.

This embodiment further includes a depth gauge 240 having a support 242 and blade 244. The support 242 includes a blade engaging end 246, a resection guide engaging end 248, and a longitudinal axis from one end to the other. The blade includes first 250 and second 252 ends and center attachment portion 254. The center attachment portion 254 is attached to the blade engaging end 246 of the support 242 with a threaded post extending from the support 242 through the attachment portion 254 and secured with a nut 255. The first 250 and second 252 blade ends are each offset a different distance from the center attachment portion 254 measured along the support 242 axis. The resection guide engaging end 248 and the resection guide 200 include an engagement mechanism for selectively attaching the depth gauge 240 to the resection guide 200. Translating jaw 222 includes a through bore 256 extending from the top surface 224 to the bottom surface 226 in communication with the guide slot 235. Depth gauge support 242 includes a hole 258 retaining a spring 260 and ball 262 plunger in the resection guide engaging end 248. The ball 262 is biased into engagement with the guide slot 235 when the resection guide engaging end 248 is inserted into through bore 256. The depth gauge can engage the through bore 256 and be supported on either the top surface 224 or bottom surface 226. When it is thus supported, the blade ends 250, 252 can be selectively placed to project over the jaws 202, 222. Each blade end projects to define a plane a different predetermined axial distance from the guide slot 235.

Figure 12:
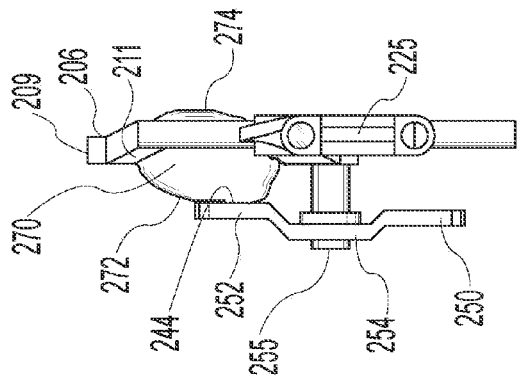
FIG. 12 is a side elevation view of the patella resection guide of FIG. 10 shown gripping a patella.
Figure 11:
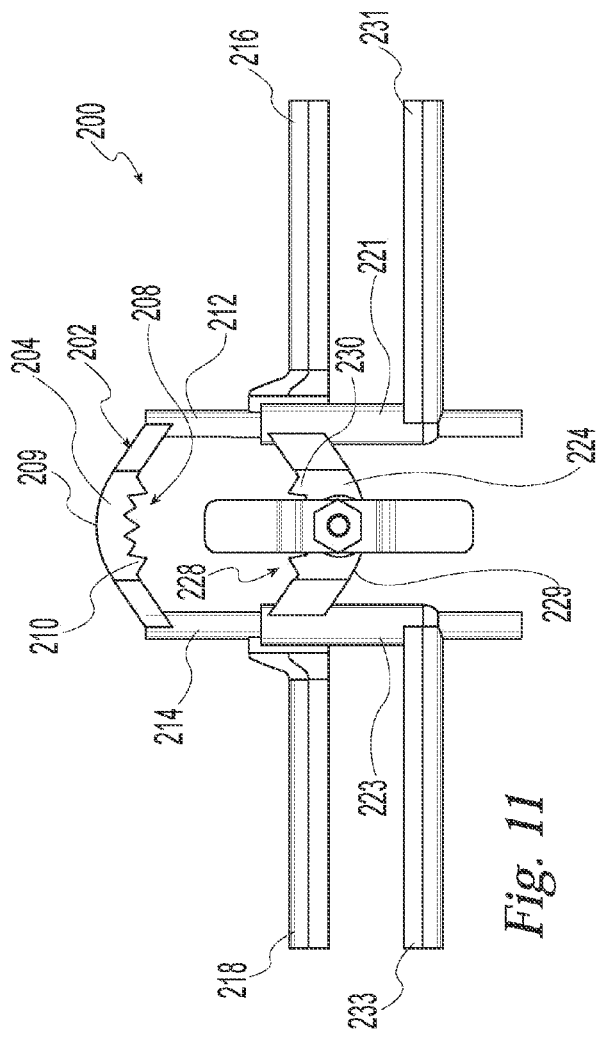
FIG. 11 is a top plan view of the patella resection guide of FIG. 10.
Figure 13:
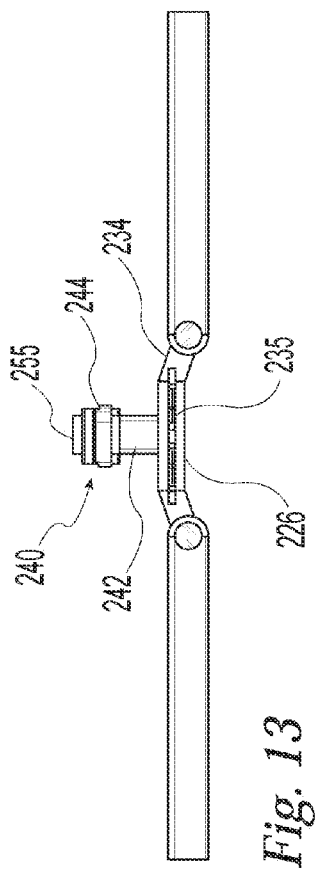
FIG. 13 is a front elevation view of the patella resection guide of FIG. 10.

Both illustrative embodiments are relatively compact to permit the stationary jaw to be wedged across the joint between the femur and patella. Both also facilitate approaching the patella from the lateral or medial side and gripping it on its sides while presenting an unobstructed side-facing saw guide slot. The use of the instrument will be described relative to the embodiment of FIGS. 10-13. The surgeon first determines whether it is desirable to remove a prescribed amount of patellar bone or to leave a prescribed amount and how much in either case. To remove a prescribed amount of bone, the depth gauge 240 is attached to the top surface 224 of the translating jaw 222 so that the blade 244 references the posterior side 272 of the patella 270 as shown in FIG. 12. To leave a prescribed amount of bone, the depth gauge 240 is attached to the bottom surface 226 of the translating jaw 222 so that the blade 244 references the anterior side 274 of the patella 270. The amount is established by positioning the blade end 250 or 252 having the corresponding amount of offset in contact with the patella. The stationary jaw 202 is wedged across the joint between the femur and patella with the top surface 204 facing toward the posterior side 272 of the patella 270 and the bottom surface 206 facing toward the femur. The patella 270 is placed between the jaws with the depth gauge blade in contact with the appropriate patellar surface and the handles 218, 233 and 216, 231 are gripped and squeezed toward one another to bring the jaws 202,222 together to grip the patella 270 medially and laterally. A saw blade is activated through the saw guide slot 235 to resect the patella. A locking mechanism can be provided to selectively prevent the jaws from moving away from one another. For example, the guide arms 212, 214 can be threaded and provided with nuts at their free ends. After the translating jaw is moved toward the stationary jaw, the nuts would be advanced to prevent the translating jaw from moving backward. Likewise, the guide arms 212, 214 can be grooved and the guide sleeves 221, 223 provided with ratcheting palls biased into engagement with the grooves such that the palls ride freely over the grooves as the jaws are moved toward one another but the palls engage the grooves and resist motion of the jaws away from one another.

The distal femur is prepared using a distal femoral cut guide. FIGS. 14-17 show an illustrative embodiment of an intramedullary (IM) distal femoral cutting instrument 300 for guiding the distal femoral cut. An IM alignment guide 302 includes a body 304 having front 306 and back 308 surfaces, lateral 310 and medial 312 ends, and first 309 and second 311 side surfaces. A through slot 314 communicates from the front surface 306 to the back surface 308. A cut guide engaging slot 316 extends part way from the back surface 308 toward the front surface 306. The cut guide engaging slot 316 is generally aligned with the through slot 314 and is wider than the slot 314 side-to-side. The cut guide engaging slot 316 extends laterally to open at the lateral end 310. A neck 318 projects from the medial end 312 and extends the back surface 308 medially. A lug 320 is connected to the end of the neck 318 opposite the body 304. The lug includes a rounded reference surface 322 that projects beyond the back surface 308. A socket 324, having a longitudinal axis, is formed in the reference surface 322. The axis of the socket 324 forms a predetermined angle relative to the back surface 308. For a medial approach to the knee, the angle will be obtuse and for a lateral approach it will be acute. An intramedullary rod 326 having a longitudinal axis fits into the socket 324 so that the rod 326 axis is coaxial with the socket axis and extends from the IM alignment guide at the predetermined angle. The rod 326 is welded in place.

An IM distal cut guide 330 includes a body 332 with front 334 and back 336 surfaces, medial 338 and lateral 340 surfaces, and first 342 and second 344 sides. Three saw blade slots 345 extend through the cut guide 330 from the medial 338 to the lateral 340 surface. The slots 345 lie in planes parallel to the front surface 334. A pin tab 346 extends from the back surface 346 and has lateral 348 and medial surfaces 350 that taper 353 inwardly from the medial 338 and lateral 340 surfaces of the body. Fixation holes 351 extend through the pin tab from the lateral surface 348 to the medial surface 350. An engagement tab 352 extends from the front surface 334 and has sides 354 and 356 and front surface 358. A threaded hole 360 extends from the front surface 358 toward the body 332. The engagement tab 352 engages the cut guide engaging slot 316 with the front surface 334 of the distal cut guide resting against the back surface 308 of the IM alignment guide such that the saw blade slots 345 are parallel to the back surface 308 and thus are at the predetermined angle relative to the IM rod 326. The plane of the middle saw blade slot intersects the extreme end of the reference surface 322. It is desirable to resect the distal femur perpendicular to the mechanical axis of the femur. Therefore, the distal cut guide is aligned such that a line perpendicular to the saw blade slots 345 is aligned with the mechanical axis. This is accomplished by providing a plurality of IM alignment guides having the angle of the IM rod 326, relative to the plane of the saw blade slots 345, equal to the difference between the anatomic and mechanical axes of the femur. Because of variation in the patient population, IM alignment guides having different rod 326 angles are provided. For example, angles of 4°, 6°, and 8° have been found to be suitable to accommodate most patients. The engagement of the tab 352 and slot 316 allows the distal cut guide 330 to slide relative to the IM alignment guide 302 from a first position in which the distal cut guide 330 is farther from the IM rod 326 and a second position in which the distal cut guide 330 is nearer to the IM rod 326. A handle 361 includes a grip portion 362, a threaded stud 363 opposite the grip portion 362, and a shoulder 364 intermediate the grip portion 362 and the threaded stud 363. The threaded stud 363 extends through the slot 314 in the IM alignment guide 302 to threadingly engage the threaded hole 360 in the engagement tab 352 of the distal cut guide 330. As the handle 361 is rotated to further engage the threaded hole 360, the shoulder 364 bears against front surface 306 of the IM alignment guide 302 and the front surface 334 of the distal cut guide 330 is drawn into tight locking engagement with the back surface 308 of the IM alignment guide 302. By means of the handle 361, the distal cut guide 330 can be slid and locked at any position of its travel along the IM alignment guide.

In use, a hole is drilled in the center of the patellar sulcus 366 of the distal femur, making sure that the hole is parallel to the shaft of the femur 365 in both the frontal and sagittal planes. The hole provides access to the IM canal of the femur 365. An IM alignment guide 302 is selected as appropriate for a medial or lateral approach and having a rod 326 angle that accounts for the difference between the anatomic and mechanical axes of the femur as determined by preoperative templating. The IM distal cut guide 330 is attached to the alignment guide 302 using the handle 361. Using the handle, IM rod 326 is inserted into the IM canal of the femur 365. The assembly is inserted until the reference surface 322 contacts the intercondylar sulcus 366 with the IM alignment guide 302 projecting toward the exposed side of the knee. The distal cut guide 330 is slid in slot 316 until the medial surface 338 is adjacent the bone. In FIG. 17, the distal cut guide 330 is shown adjacent the medial condyle 367. The handle 360 is rotated to lock the distal cut guide 330 relative to the IM alignment guide 302. Pins 368 are then inserted through the holes 351 in the pin tab 346 and into the bone to hold the distal cut guide 330 in place. The taper 353 of the medial side 350 of the pin tab 346 causes it to fit the condylar bone more closely and therefore more stably. Once the pins are placed, the handle 361 is unthreaded from the distal cut guide 330 and the IM alignment guide 302 and IM rod 326 are removed from the bone leaving the distal cut guide 330 pinned to the bone. A saw blade is then directed through one of the slots 345 to resect the distal femur. If the reference surface 322 was fully seated in the intercondylar sulcus 366, the middle saw guide slot will resect the distal femur to the depth of the sulcus. The other slots provide more or less resection.

Figure 18:
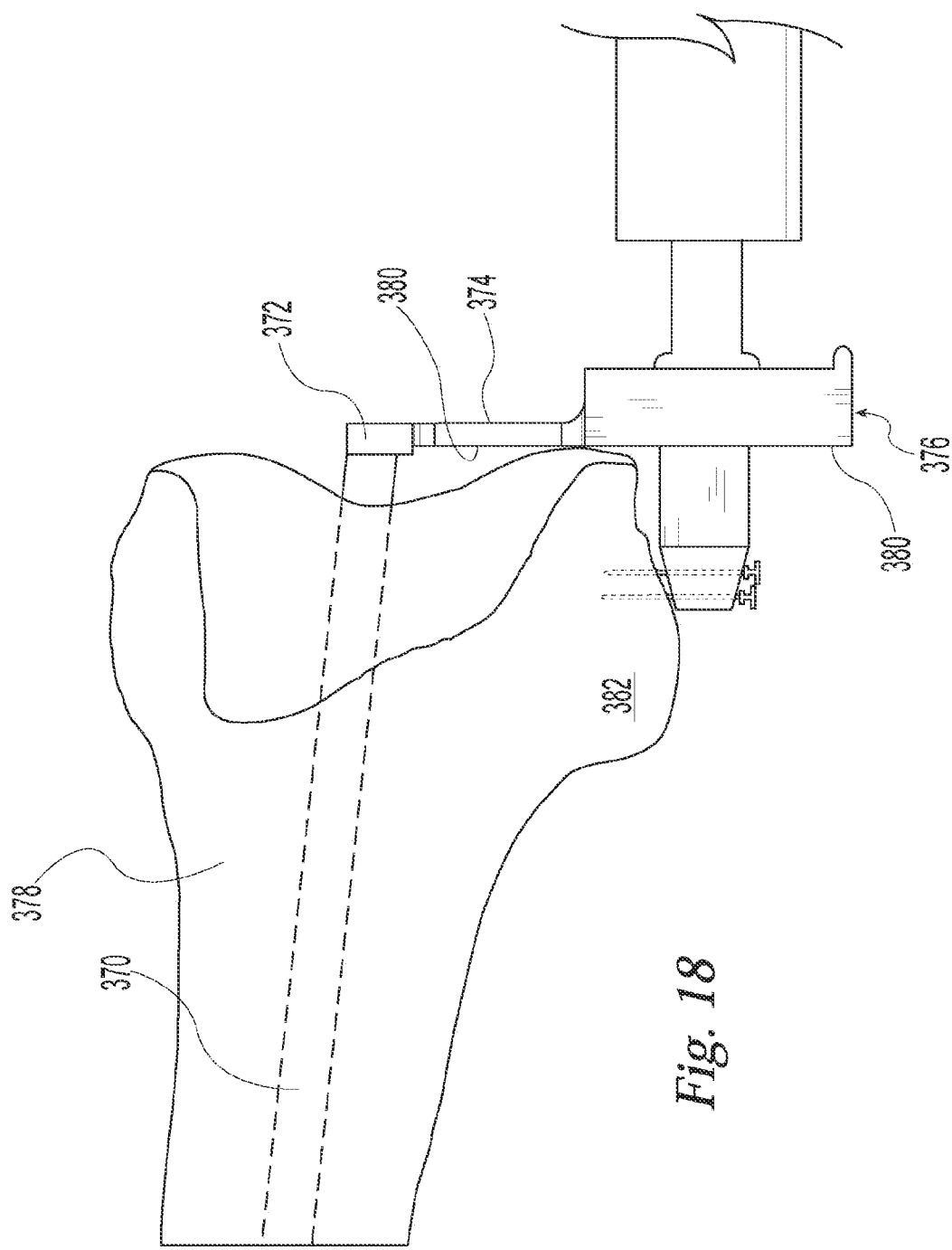
FIG. 18 is a side elevation view of another illustrative intramedullary distal femoral cutting instrument according to the present invention mounted on a femur.

FIG. 18 shows an alternative embodiment of distal femoral cut guide 300 in which the lug 320 and rounded reference surface 322 have been omitted. Instead, an IM rod 370 is connected directly to the end 372 of the neck 374 of the IM alignment guide. In this embodiment, the IM rod 370 is inserted into the IM canal of the femur 378 until the back surface 380 contacts the near distal femoral condyle. In this case the back surface 380 contacts the distal medial condyle 382. The plane of the middle saw blade slot is offset 10 mm from the back surface 380. The other slots are offset 6 mm and 14 mm respectively. Thus, the appropriate slot is chosen based on how much bone is to be resected from the distal femur relative to the near condyle. Typically, the middle or 10 mm slot would be used with a medial approach and less would be used with a lateral approach.

Figure 22:
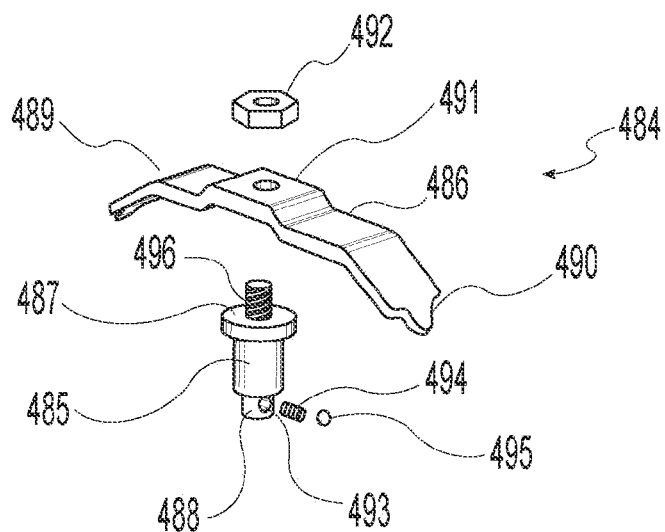
FIG. 22 is an exploded perspective view of an illustrative embodiment of a depth gauge for use with the tibial cut guide of FIG. 19 according to the present invention.
Figure 23:
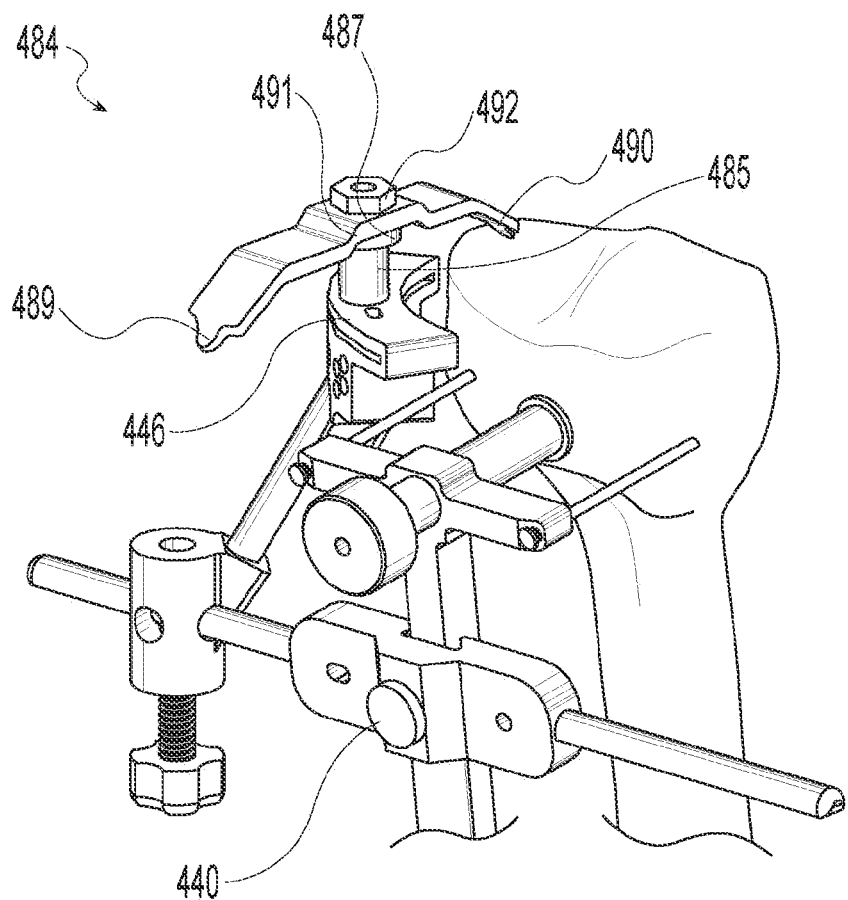
FIG. 23 is a perspective view of the tibial cut guide assembly of FIG. 19 and the depth gauge of FIG. 22 mounted on a tibia.
Figure 29:
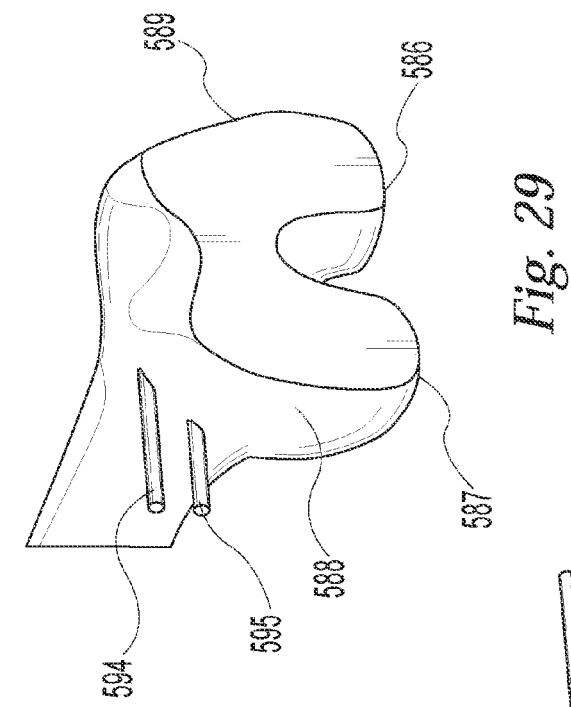
FIG. 29 is a perspective view showing two reference pins inserted in the distal femur using the femoral A/P sizer and pin guide assembly of FIG. 24.
Figure 28:
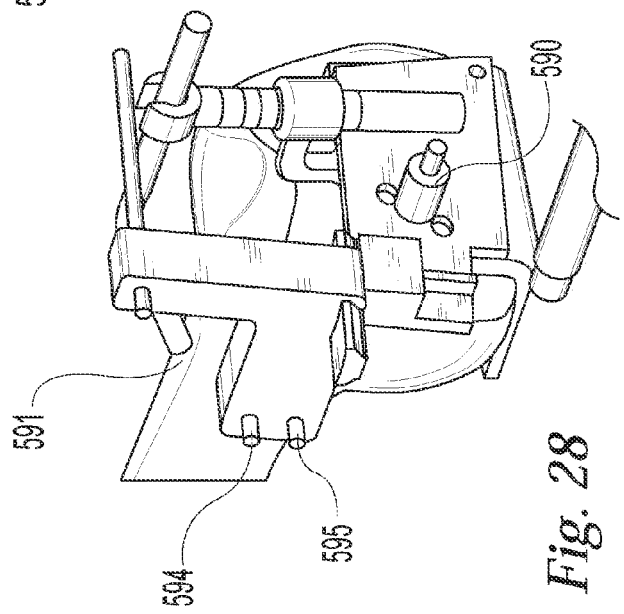
FIG. 28 is a perspective view showing the femoral A/P sizer and pin guide assembly of FIG. 24 fully assembled on a distal femur.
Figure 27:
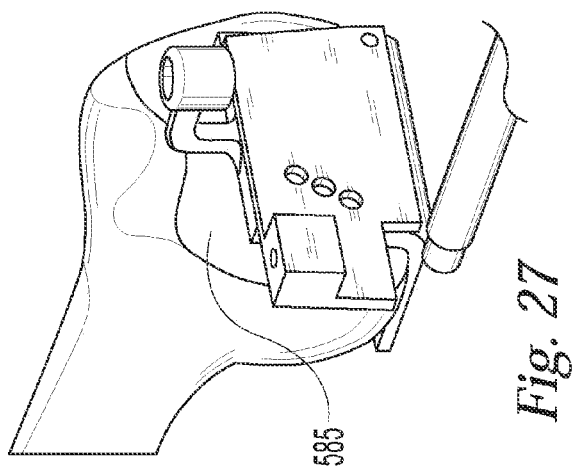
FIG. 27 is a perspective view showing the femoral A/P sizer and pin guide assembly of FIG. 24 being assembled on a distal femur.

The proximal tibia is prepared using a tibial cut guide. FIGS. 19-23 show an illustrative embodiment of a tibial cut guide assembly 400 for guiding the proximal tibial cut. The assembly includes a tibial tubercle alignment bar 402, a tibial boom 430, a tibial cut guide 446, and a tibial depth gauge 484 (FIGS. 22-23). The tibial tubercle alignment bar 402 includes an elongate body 404 having an anterior face 406, a posterior face 408, first and second side walls 410, 412, a distal end 414, a proximal end 416, and a longitudinal axis running from the distal end to the proximal end. A dovetail 417 is formed on a portion of the alignment bar 402 adjacent the anterior face 406. A stop 418 projects from the anterior face 406 near one end of the dovetail 417 toward the distal end 414 of the alignment bar 402. Extensions 420 project perpendicularly from either side 410, 412 of the body 404 near the proximal end 416. Fixation holes 421 are formed through the extensions 420 from anterior to posterior for receiving fixation pins. A threaded bore 422 extends through the alignment bar 402 from the anterior face 406 to the posterior face 408 near the proximal end 416. A plunger 424 having a threaded shaft 426 and an adjustment knob 427 is received in the threaded bore 422 such that rotating the adjustment knob 427 moves the plunger 424 anteriorly and posteriorly to change the spacing from the end of the plunger 424 to the posterior face 408. A cannula 428 extends through the plunger 424, shaft 426, and knob 427 to allow a pin to pass.

A tibial boom 430 includes a body 431 having an anterior face 432, a posterior face 433, a proximal end 434, a distal end 435, and first and second sides 436, 437. A boss 438 projects from the anterior face and a dovetail groove 439 is formed into the posterior face. A threaded bore is formed through the boss 438 from the anterior face 432 to the dovetail groove 439. A set screw 440 is received in the threaded bore such that rotating the set screw 440 moves it into and out of the dovetail groove 439. Extension bars 442 extend from the first and second sides 436, 437. The extension bars 442 are "D"-shaped in that they are generally cylindrical with a flat 443 along one side. The extension bars 442 define a longitudinal axis along their length that is perpendicular to the dovetail groove 439. The tibial boom 430 is mounted on the alignment bar 402 with the dovetail groove 439 engaging the alignment bar dovetail 417 such that the boom 430 can translate along the longitudinal axis of the alignment bar between a first position nearer the proximal end 416 of the alignment bar 402 and a second position further from the proximal end 416 of the alignment bar 402. The set screw 440 is operable to lock the tibial boom 430 in place by turning the set screw 440 so that it moves into the dovetail groove 439 to engage the dovetail 417. When the tibial boom is unlocked, it can slide freely distally until it abuts the stop 418 which prevents it from sliding further distally. In this way, the tibial boom 430 can be left unlocked and resting against the stop 418 ready to be moved into position. The longitudinal axis of the tibial tubercle alignment bar 402 and the longitudinal axis of the extension bars 442 together define a guide plane.

A tibial cut guide 446 includes a cutting head 448 having a proximal face 450, a distal face 452, opposite side faces 454, 456, a concave posterior face 458, and a convex anterior face 460. A saw guide slot 462 extends through the cutting head 448 from the anterior face 460 to the posterior face 458 generally parallel to the proximal face 450. Fixation holes 464, 466 also extend through the cutting head 448 from anterior to posterior. The smaller holes 464 are sized to receive conventional fixation pins, while the larger hole 466 is sized to receive a spring pin. Proximal face 450 includes a through bore 468 extending from the proximal face 450 to at least the saw guide slot 462 for receiving a depth gauge. In the illustrative embodiment, the bore 468 extends all the way through the cutting head 448 to ease assembly and cleaning. The cutting head 448 is supported on a base 472 by a leg 474. The base 472 is a cylinder having a longitudinal axis and proximal 471 and distal 473 faces. Two pairs of "D"-shaped transverse bores 480, 482 extend through the base 472 perpendicular to its longitudinal axis, the flat portion of the "D"-shaped holes also being perpendicular to the base axis. A threaded axial bore 476 in the distal face 473 communicates with the path of the "D"-shaped holes 480, 482 and receives a set screw 478. The leg 474 attaches to the base 472 adjacent the proximal face 471 and angles away from the base 472 to support the cutting head 448 in a position offset from the base 472 axis with the saw guide slot 462 defining a cutting plane perpendicular to the longitudinal axis of the base 472.

The tibial cut guide 400 is provided with a depth gauge 484 having a support 485 and a blade 486. The support 485 includes a blade engaging end 487, a resection guide engaging end 488, and a longitudinal axis from one end to the other. The blade 486 includes first 489 and second 490 ends and a center attachment portion 491. The center attachment portion 491 is attached to the blade engaging end 487 with a threaded post 496 extending from the support 485 through the attachment portion 491 and secured with a nut 492. The first 489 and second 490 blade ends are each offset a different distance from the center attachment portion 491 measured along the support 485 axis. The depth gauge support 485 includes a hole 493 retaining a spring 494 and ball plunger 495. The ball 495 is biased into engagement with the guide slot 462 when the resection guide engaging end 488 is inserted into the through bore 468. When it is thus supported, the blade ends 489, 490, can be selectively positioned to project posteriorly over a tibial bone. Each blade end projects to define a point a different predetermined axial distance above the saw guide slot 462.

The tibial cut guide 446 is assembled to the tibial boom 430 by sliding one of the "D"-shaped extension bars 442 through one pair 482 of the "D"-shaped holes 480,482. One pair of holes 482 provides for a left knee medial/right knee lateral orientation while the other 480 provides for a left knee lateral/right knee medial orientation. Thus assembled, the cutting head 448 is supported in a position proximal and posterior to the base 472. The set screw 478 can be tightened until it engages the flat 443 of the extension bar 442 to lock the cut guide 446 in position on the extension bar 442. Thus locked, the longitudinal axis of the base 472 is perpendicular to the flat 443 of the extension bar 442 resulting in the saw guide slot 462 being parallel to the flat 443. The angle of the flat 443, and thus the saw guide slot, relative to the guide plane defined by the alignment bar 402 and extension bar 442 axes is the posterior slope angle of the tibial cut guide assembly 400. Tibial booms 430 providing varying degrees of posterior slope may be provided. For example, having two booms 430, one with the flat 443 rotated 3° and the other with the flat rotated 7° would allow the surgeon to choose to cut the tibia with 3° or 7° of posterior slope.

In use, a tibial boom 430 is selected having the desired posterior slope angle. The tibial boom is assembled to the alignment bar 402 and allowed to slide all the way down to rest on the stop 418. The plunger 424 is positioned proximal of the tibial tubercle and centered mediolaterally with the medial third of the tibial tubercle. A pin is inserted through the cannula 428 of the plunger 424 to stabilize the alignment guide. Alternatively, a pin can be placed proximal of the tibial tubercle and centered mediolaterally with the medial third of the tibial tubercle and the cannula 428 then slipped over the pin until the plunger 424 contacts the patient. The distal end 414 of the alignment bar 402 is adjusted mediolaterally so that the guide is aligned with the mechanical axis of the tibia. In the sagittal plane, the alignment bar 402 is adjusted so that it is parallel to the anterior tibial shaft. Proximally, this adjustment is made by turning the knob 427 to move the plunger 424 anterioposteriorly. Additional pins are placed through fixation holes 421 to further secure the alignment bar 402. This establishes the position of the guide plane relative to the tibia. Now, as the tibial cut guide 446 is positioned along the boom 430 and the boom is adjusted up and down, the saw guide slot 462 will be constrained to parallel planes of posterior slope having the same angular relation to the guide plane. Thus, the tibial cut guide 446 can now be adjusted medial-laterally and proximal-distally without changing the varus-valgus orientation or the posterior slope of the resection plane.

The tibial cut guide 446 is assembled to the tibial boom using the appropriate pair of holes 480, 482 for medial/lateral orientation of the cut guide 446. The tibial depth gauge 484 is inserted into the top of the tibial cut guide 446 with the blade end 489, 490 corresponding to the desired resection level oriented over the tibia. The tibial cut guide 446 is positioned by moving the tibial boom 430 vertically until the depth gauge 484 references the desired spot on the tibial surface and sliding the cut guide medial-laterally on the extension bar 442 so that it is adjacent the tibia. This position is maintained by tightening the boom set screw 440 and the cut guide set screw 478. Pins and/or screws can then be placed in fixation holes 464, 466 to stabilize the tibial cut guide. The depth gauge is removed and a saw blade is inserted through the saw guide slot 462 to cut the proximal surface of the tibia.

FIGS. 24-29 show an illustrative embodiment of a femoral A/P sizer assembly 500 for determining femoral anterior/posterior (A/P) size and placing reference datums for guiding the femoral box cuts. The assembly includes an A/P sizer base 502, an external rotation plate 525, an A/P sizing tower 540, an anterior boom 550, a drill guide slide 560, a parallel pin drill guide 570, and an alignment pin 579. The A/P sizer base 502 includes a plate-like body 503 having a front surface 504, a back surface 505, an anterior edge 506, a posterior edge 507, and side surfaces 508,509. Posterior condyle referencing feet 510, 511 extend perpendicularly from the front surface 504 and define a posterior reference plane with their top surfaces 512 and 513. Internally threaded boss 514 projects from one side 508 of the sizer base 502 to threadably receive a handle 515. Three alignment holes 516 extend through the sizer base 502 from the front surface 504 to the back surface 505. A countersunk pivot pin hole 517 extends through the sizer base 502 from the front surface 504 to the back surface 505. An anterior extension 518 projects from the anterior edge 506 to support a hollow, cylindrical tower bushing 519 having a top surface 521 and a bore 520 with a longitudinal axis parallel to the front and back surfaces 504, 505 and perpendicular to the posterior condyle referencing feet 510, 511. A through hole in the side of the tower bushing 519 receives a set screw 522 in communication with the bore 520.

An external rotation plate 525 includes a plate-like body 526 having a front surface 527 a back surface 528, an anterior edge 529, a posterior edge 530, and side surfaces 531, 532. A drill slide bushing 533 is connected to, and projects from, one side 532 of the external rotation plate 525. The drill slide bushing 533 includes a "D"-shaped bore 534 having a longitudinal axis parallel to the front surface 527. A through hole in the side of the drill slide bushing 533 threadably receives a set screw 524 in communication with the flat side of the "D"-shaped bore. Three, alignment holes 535 extend through the external rotation plate 525 from the front surface 527 to the back surface 528. A pivot pin hole 536 extends through the external rotation plate 525 from the front surface 527 to the back surface 528.

The external rotation plate 525 is mounted on the A/P sizer base 502 with the external rotation plate front surface 527 flat against the sizer base back surface 505. A pin 537 secured in the pivot pin holes 517, 536 holds the assembly together and permits planar rotation of the external rotation plate 525 relative to the sizer base 502. The alignment holes 516, 535 are positioned so that a pair of holes aligns when the external rotation plate 525 is rotated relative to the sizer base 502 at each of 3°, 5°, and 7° as measured between a line perpendicular to the top surfaces 512, 513 of the posterior condyle referencing feet 510, 511 and the drill slide bushing 533 axis.

A femoral A/P sizing tower 540 includes a shaft 541 having a first end 542, a second end 543, and a longitudinal axis extending from the first end to the second end. A collar 544, connected to the second end 543 of the sizing tower 540, includes a through hole 545 having an axis perpendicular to the longitudinal axis of the shaft 541. A keyway 546 is cut in the side of the collar 544 opposite the shaft 541. Femoral A/P size indicia 547 are inscribed on the shaft 541. The sizing tower 540 is mounted on the A/P sizer base 502 with its shaft 541 slidably received within the tower bushing 519 in coaxial relation such that the sizing tower 540 is free to slide up and down, and rotate about, their coincident axes. An anterior boom 550 includes a handle 551 and a shaft 552 having a common longitudinal axis. A probe 553 extends beyond the shaft 552 and bends away from the shaft axis to a probe tip 554 that is offset a predetermined distance from the shaft 552 axis. A key 555 extends longitudinally from the handle 551 and overlies a portion of the shaft 552. The anterior boom 550 is mounted in the collar 544 of the sizing tower 540. The diameter of the probe 553 is smaller than the keyway 546 and the diameter of the shaft 552 fits closely with the through hole 545. Thus, the anterior boom 550 can be mounted by moving the probe 554 down through the keyway 546 and then sliding the shaft 552 into of the through hole 545. As the shaft 552 is slid into place, the key 555 engages the keyway 546 to prevent the anterior boom 550 from rotating about its shaft 552 axis. The handle 551 abuts the collar 544 to prevent the anterior boom 550 from further translating along its shaft axis. Thus mounted, the probe tip 554 is in a predetermined position relative to the indicia 547 of the sizing tower 540. As the sizing tower 540 is moved up and down in the tower bushing 519, the probe tip 554 moves up and down in known relation to the top surfaces 512, 513 of the posterior condyle referencing feet 510, 511. This relationship is indicated by the position of the indicia 547 adjacent the top surface 521 of the tower bushing 519. The sizing tower 540 can be locked in position within the tower bushing bore 520 by tightening the set screw 522.

A drill guide slide 560 includes a base 561 having a dovetail profile 562 defining a longitudinal dovetail axis. A support arm 563 extends from the base 561 perpendicular to the dovetail and the dovetail axis. The support arm 563 is "D"-shaped, being generally cylindrical with one side milled flat 564. The support arm 563 is received in the bore 534 of the drill slide bushing 533 for sliding movement along the bore axis. The "D"-shape of the arm 563 and bore 534 prevents the arm from rotating. The support arm 563 can be locked axially within the bore 534 by tightening the set screw 524 so that it bears against the flat 564.

A parallel pin drill guide 570 includes a body 571 having top 572, bottom 573, front 574, back 575, and side 576, 577 surfaces. A dovetail groove 592, having a longitudinal dovetail groove axis, is formed from side-to-side in the bottom surface 573. Drill guide holes 593 extend through the body 571 from side-to-side. The guide holes 593 each have a longitudinal axis that is parallel to the other and parallel to the longitudinal axis of the dovetail groove 592. An anterior alignment hole 578 extends through the body 571 from side-to-side to receive an alignment pin 579. The parallel pin drill guide 570 is mounted on the drill guide slide 560 with the base dovetail 562 engaging, and coaxially aligned with, the dovetail groove 592 so that the parallel pin drill guide 570 can slide along the coincident axes. Thus assembled, the guide hole 593 axes are parallel to the front surface 504 of the A/P sizer base and they are at an angle relative to the top surfaces 512, 513 of the posterior condyle referencing feet 510, 511 as determined by the rotated position of the external rotation plate 525. The alignment pin 579 can be extended over the shaft 552 of the anterior boom 550 to act as a feeler gauge to reference the vertical position of the drill guide 570 to the vertical position of the probe tip 554. By adjusting the parallel pin drill guide up and down until the alignment pin 579 rests on the shaft 552, the guide holes 593 can be positioned at a predetermined position relative to the probe tip 554. In this illustrative embodiment, the A/P sizer base 502 and the external rotation plate 525 are hinged on the lateral side in order to adjust external rotation. Also in this illustrative embodiment, only one drill slide bushing 533 (medial or lateral) is provided on each external rotation plate 525. Because of this design, four A/P sizer base 502 and external rotation plate 525 combinations would be provided to allow for medial and lateral approaches to both a left and a right knee.

In use, the handle 515 is assembled to the appropriate A/P sizer 500 depending on whether the operative knee is left or right and whether the approach is medial or lateral. In the illustrative embodiment, the A/P sizer 500 is placed so that the front surface 504 of the A/P sizer base is flat against the resected distal femur 585 and the top surfaces 512, 513 of the feet 510, 511 are flush against the posterior condyles 586, 587. Alternatively, the A/P sizer could be placed on an unresected femur and the distal femoral cut made later. In such a case, the distal cut depth could also be set with the A/P sizer. The A/P sizer 500 offers three methods for setting external rotation: the epicondylar axis, the A/P axis, or the posterocondylar axis. To use the epicondylar axis, a line is drawn between the medial and lateral epicondyles 588, 589. The feet 510, 511 are placed against the posterior condyles 586, 587 and the anterior edge 529 of the external rotation plate 525 is then set parallel to the line drawn between the epicondyles 588, 589. The pair of alignment holes 516, 535 that most nearly align are then aligned and the sizer 500 is secured by inserting a spring pin 590 through the aligned holes 516, 535. Likewise, to use the A/P axis, Whiteside's line is drawn along the A/P axis. The feet 510, 511 are placed against the posterior condyles 586, 587 and the anterior edge 529 of the external rotation plate 525 is then set perpendicular to the line drawn along the A/P axis. The pair of alignment holes 516, 535 that most nearly align are then aligned and the sizer 500 is secured by inserting a spring pin 590 through the aligned holes 516, 535. To use the posterior condylar axis, the appropriate set of alignment holes 516, 535 are aligned to correspond to 3°, 5°, or 7° of external rotation while the feet 510, 511 are kept against the posterior condyles 586, 587 and a spring pin 590 is inserted through the aligned holes.

Once rotation is established, the A/P sizing tower 540 is inserted into the tower bushing 519. The anterior boom 550 is inserted into the collar 544 with the key 555 engaging the keyway 546. The probe tip 554 is positioned on the anterior cortex 591 of the femur. The position of the probe tip 554 will determine the exit point of the anterior bone cut and the ultimate position of the femoral joint component. The vertical position of the A/P sizing tower 540 is locked by tightening the set screw 522. The femoral size is indicated by the indicia 547 appearing above the top surface 521 of the tower bushing 519. The drill guide slide 560 is mounted in the drill slide bushing 533 and the parallel pin drill guide 570 is mounted on the drill guide slide 560. The alignment pin 579 is inserted through the anterior alignment hole 578. The drill guide 570 and drill guide slide 560 are raised until the alignment pin 579 rests on top of the shaft 552 to set the A/P position of the femoral component. The vertical position of the drill guide slide 560 is locked by tightening the set screw 524. The drill guide 570 is slid along the drill guide slide 560 until it is adjacent the femur. A hole is drilled into the femur through one of the guide holes 593 and a headless pin 594 is placed in the drilled hole to establish a datum that records the rotation angle and A/P position in such a way that the datum can be subsequently referenced by bone cutting guides to produce bone cuts relative to the rotation and position information. The illustrative embodiment describes using pins set in the femur as datums. Other datums that can record the information are contemplated and include by way of example: one or more holes, screws, notches, and grooves. A single pin can record the external rotation and A/P position. However, rotation about the pin axis is not constrained by a single pin without some other reference such as the distal femur. If desired, a second hole can be drilled into the femur through the other guide hole 593 and a second headless pin 595 placed to constrain rotation about the pin axes and also to provide a more stable datum. All components of the A/P sizer assembly 500 are now removed leaving the headless pins 594, 595 in place to locate the femoral profile cut.

Figure 32:
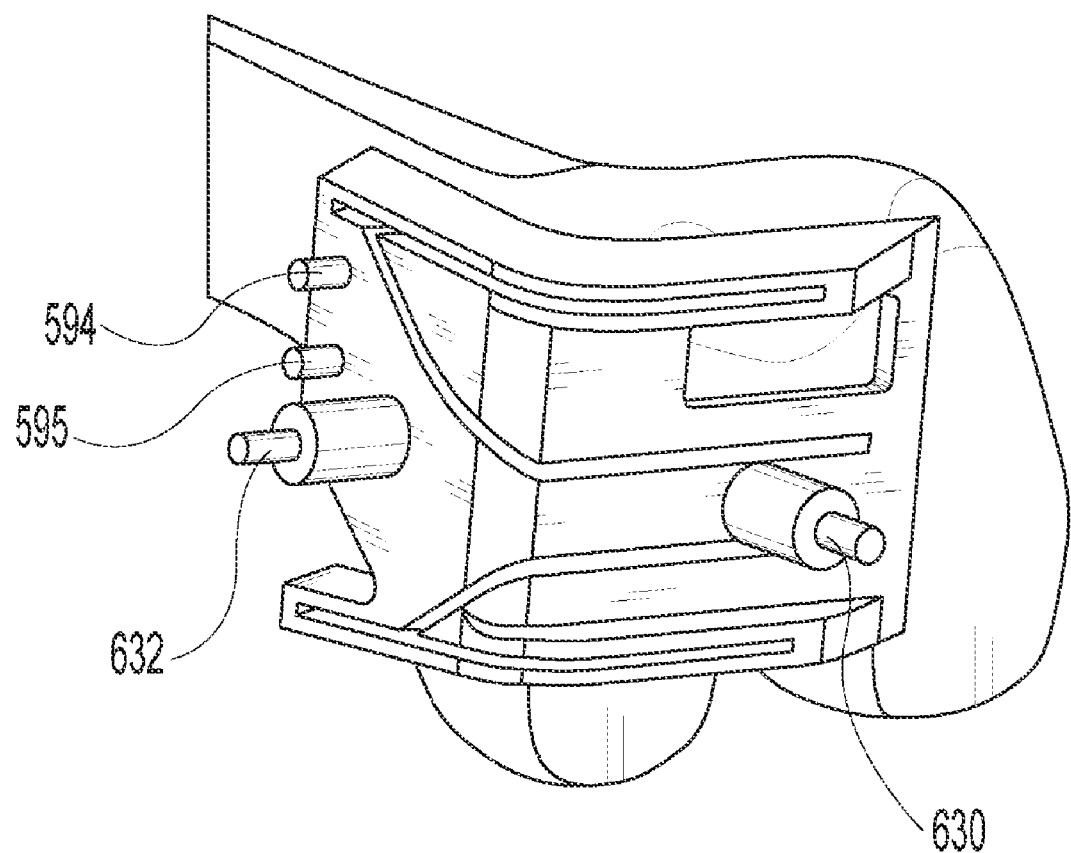
FIG. 32 is a perspective view of the femoral profile cut block of FIG. 30 mounted on a femur.

The femoral box cuts, or profile, are cut using a femoral profile cut block. FIGS. 30-32 show an illustrative femoral profile cut block 600 for guiding the anterior, posterior and chamfer cuts on the distal femur. The cut block 600 is generally an "L"-shaped body having inner 602 and outer 604 distal surfaces, inner 606 and outer 608 side surfaces, an anterior surface 610, and a posterior surface 612. A pair of pin reference holes 614 extends through the side of the cut block 600 from the outer side surface 608 to the inner side surface 606 for receiving the headless femoral reference pins 594, 595. The reference holes 614 are elongated proximal-to-distal to allow proximal-to-distal motion relative to a reference pin while still constraining the A/P position and external rotation relative to the pin. This arrangement allows the proximal-to-distal position of the block 600 to be referenced from the distal surface 602 rather than the holes 614. A side fixation hole 616 extends through the side of the cut block 600 from the outer side surface 608 to the inner side surface 606 for receiving a fixation pin. A distal fixation hole 618 extends through the distal side of the cut block 600 front the outer distal surface 604 to the inner distal surface 602 for receiving a fixation pin. Anterior 620, anterior chamfer 622, posterior 624, and posterior chamfer 626 saw guide slots corresponding to the anterior, posterior, and chamfer surfaces of a femoral implant box are positioned in fixed predetermined relationship to the pin reference holes 614. The slots sweep around the cut block 600 from the side surfaces to the distal surfaces to permit a saw blade to be directed medial-laterally and proximal-distally to make a complete cut across the femur through each slot. A visualization window 628 extends from the outer distal surface 604 to the inner distal surface 602 to allow direct visualization of the distal femur during positioning of the cut block 600 and cutting of the distal femur. When surgery is performed through a small surgical incision, this window 628 permits the surgeon to observe the saw blade in action. The medial side of the instrument is contoured to match the incision by providing a notch 629 to provide soft tissue clearance for the illustrative minimally invasive surgical procedure. For a lateral approach, a cut block is provided with the lateral side contoured to match the incision.

Figure 33:
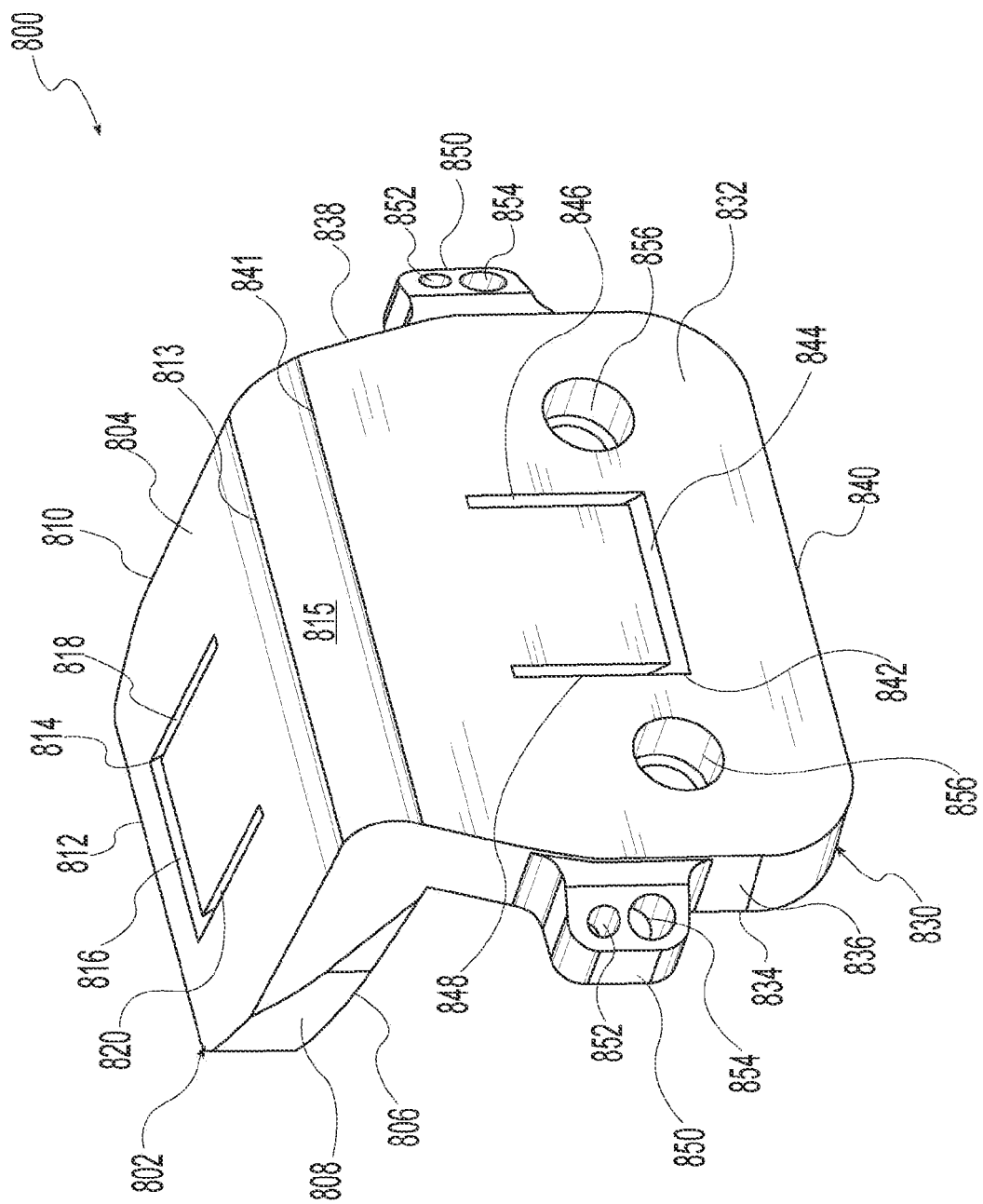
FIG. 33 is a perspective view of an illustrative embodiment of a trochlear cut guide according to the present invention.

In use, the appropriate size femoral profile cut block 600 is positioned over the headless pins 594, 595 with the pins engaging pin reference holes 614 which sets the A/P position and external rotation of the cut block 600. The cut block 600 is secured to the femur with a spring pin 630 through the distal fixation hole 618. As the pin 630 is tightened, the cut block 600 can move proximally due to the elongated holes 614 until the inner distal surface 602 is stably seated on the distal femur. An additional spring pin 632 can be inserted from the side through the side fixation hole 616 to further stabilize the cut block 600. A saw blade can now be used to cut the femoral profile by directing it through the posterior 624, posterior chamfer 626, anterior 620, and anterior chamfer 622 saw guide slots. The cuts can be made in any order; however, by making them in this order optimal stability of the cut guide can be maintained. After the cuts are made, the cut block and headless pins are removed.

Where required, a trochlear recess or notch is cut using a trochlear notch guide. This would be required when a femoral implant has a trochlear recess or notch that extends into the anterodistal portion of the femoral box profile. For example, in an implant where a deeper patellar groove is incorporated, extra material may be added to the inside of the implant to accommodate the deeper groove. Consequently, a cutout must be formed on the bone to receive this extra material for a conforming fit between the implant and bone. FIG. 33 shows an illustrative embodiment of a trochlear cut guide 800. The trochlear cut guide 800 comprises a generally "L"-shaped body including an anterior portion 802 having an external anterior surface 804, an internal anterior surface 806, opposing sides 808, 810, a proximal side 812, and a distal side 813. An anterior chisel guide slot 814 extends through the anterior portion 802 from the external anterior surface 804 to the internal anterior surface 806. The chisel guide slot 814 comprises a proximal slot opening 816 and two side slot openings 818, 820. A distal guide portion 830 extends at an angle from the distal side 813 of the anterior portion 802. The distal portion 830 includes an external distal surface 832, an internal distal surface 834, opposing sides 836, 838, a posterior side 840, and an anterior side 841. The anterior side 841 of the distal portion 830 and the distal side 813 of the anterior portion 802 blend at a radius 815 to form the connection between these two portions. A distal chisel guide slot 842 extends through the distal portion 830 from the external distal surface 832 to the internal distal surface 834. The chisel guide slot 842 comprises a posterior slot opening 844 and two side slot openings 846, 848. Ears 850 extend from each side 836, 838 of the distal portion 830. The ears 850 include fixation holes 852 and 854. Distal drill guide holes 856 guide a drill for making peg receiving holes in the distal femur. The chisel guide slots 814, 842 are aligned with the proximal slot opening 816 being coplanar with the posterior slot opening 844 and the anterior portion side slot openings 818, 820 being coplanar with the distal portion side slot openings 846, 848. A cutting instrument inserted into distal chisel guide slot 842 will exit anterior chisel guide slot 814 and cut a notch across the anterodistal aspect of the femur.

Figure 34:
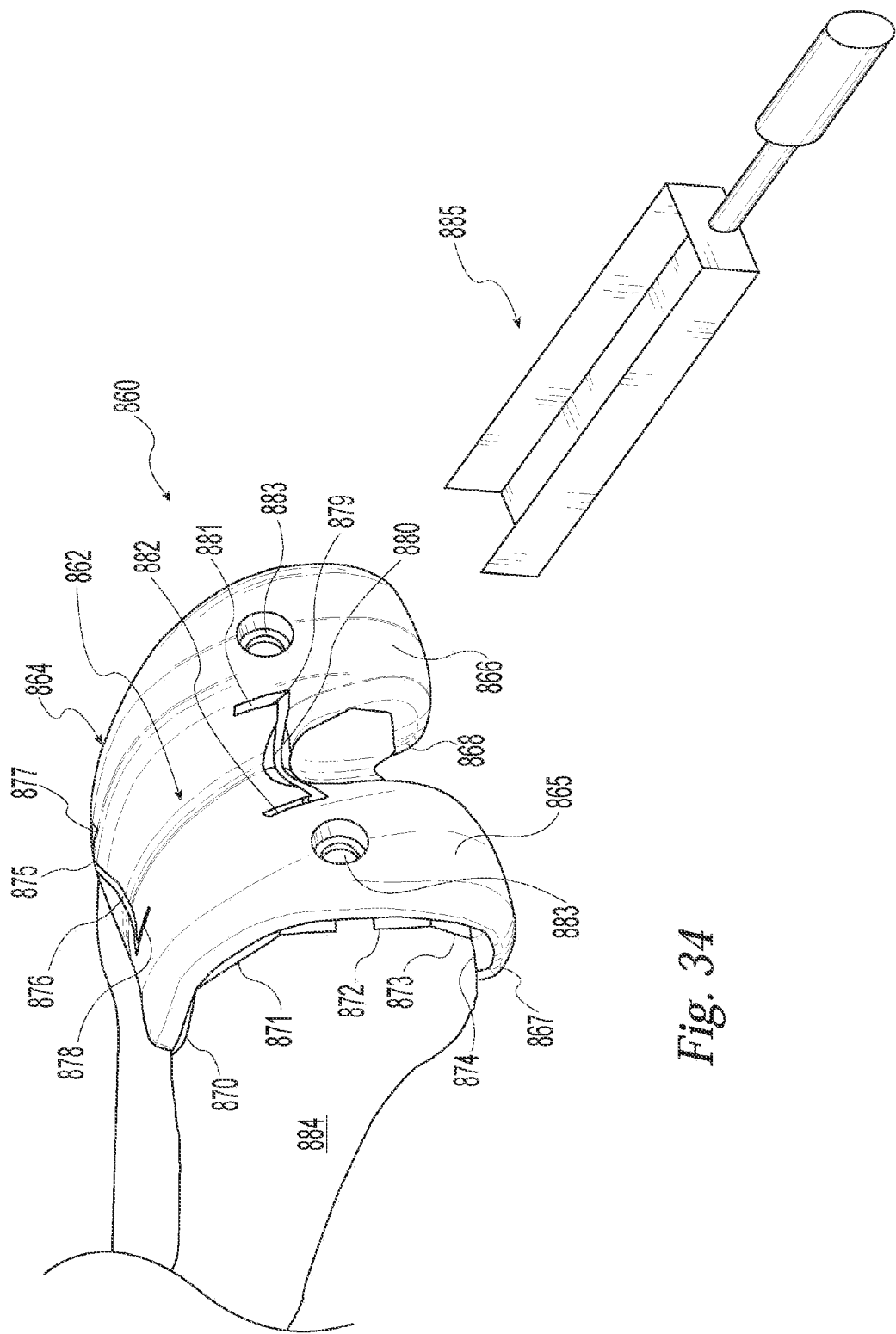
FIG. 34 is a perspective view of another illustrative embodiment of a femoral provisional trochlear cut guide according to the present invention mounted on a femur and further showing an illustrative embodiment of a chisel for use with the cut guide.

FIG. 34 shows an alternative embodiment of a trochlear cut guide comprising a slotted femoral provisional 860. This trochlear cut guide facilitates making the trochlear notch cut and drilling the distal peg holes in similar fashion as trochlear cut guide 800. However, the slotted provisional 860 includes an external articulating surface that matches the external articulating surface of a corresponding femoral implant. This permits the option of finishing the tibial and patellar cuts and conducting a trial reduction in which provisional implants of all of the knee components are inserted and flexed through their range of motion to check implant sizing and function. The mediolateral position of the slotted femoral provisional 860 can be adjusted and retested before making the trochlear notch cut and drilling the distal peg holes which set the mediolateral position. The slotted provisional 860 articular surfaces include an anterior patellar flange 864 connecting arcuate, spaced apart distal 865, 866 and posterior 867, 868 condyles. Opposite the articulating surfaces are the internal box surfaces including anterior 870, anterior chamfer 871, distal 872, posterior chamfer 873, and posterior 874 box surfaces. An anterior chisel guide slot 875 extends through the anterior flange 864 from the external anterior surface to the internal anterior box surface 870. The chisel guide slot 875 comprises a proximal slot opening 876 and two side slot openings 877, 878. A distal chisel guide slot 879 extends through the distal condyles 865, 866 from the external distal surface to the internal distal box surface 872. The distal chisel guide slot 879 comprises a posterior slot opening 880 and two side slot openings 881, 882. Distal drill guide holes 883 guide a drill for making peg receiving holes in the distal femur. Anterior chisel guide slot 875, distal chisel guide slot 879, and drill guide holes 883 are configured and function like those of the trochlear cut guide 800 of FIG. 33.

The use of the trochlear notch cutting guide will be described with reference to the slotted provisional embodiment 860 of FIG. 34. The appropriate size femoral provisional is placed on the end of the femur 884. The appropriate mediolateral position can be established visually or, in the case of the slotted provisional 860, by trial reduction. A hole is drilled into the distal femur through one of the drill guide holes 883 and a holding peg (not shown) is inserted. A hole is drilled into the femur through the other one of the drill guide holes 883 and another holding peg is inserted. A chisel 885 having a three sided blade configured to engage the chisel guide slots 875, 879 is inserted into the distal chisel guide slot 879. The chisel 885 is driven across the distal femur to engage the anterior chisel guide slot 875 and cut the trochlear notch.

Posterior stabilized femoral components have a protruding cam box. A piece of bone is cut from the intercondylar region of the distal femur using an intercondylar notch guide to accommodate this cam box. FIGS. 35-36 show an illustrative embodiment of an intercondylar notch guide 900. The notch guide 900 comprises a generally "L"-shaped body including an anterior portion 901 having an anterior outer surface 902 and an anterior inner surface 904. Spaced apart condylar portions 906, 908 depend at an angle from the anterior portion 901 to define a "U"-shaped opening 907 between them. The condylar portions have distal inner 910 and outer 912 surfaces. A trochlear ramp 914 projects from the anterior inner surface 904. The ramp 914 has a planar, distal saw guide surface 916 that intersects the anterior outer surface 902 and defines the closed end of the "U"-shaped opening 907. The condylar portions 906, 908 have parallel, spaced apart, inner side walls 918, 920. The side walls 918, 920 define medial and lateral saw guide surfaces perpendicular to distal saw guide surface 916. Each of the condylar portions 906, 908 includes a threaded peg hole 922, 924. Pegs can optionally be threaded into the holes to extend from the distal inner surface 910. In use, the appropriate size intercondylar notch guide 900 is chosen and placed on the distal femur. The trochlear ramp 914 fits within the trochlear notch cut in the prior step to position the notch guide mediolaterally. Additionally, pegs can be threaded into peg holes 922, 924 to align mediolaterally with the femoral peg holes drilled in the prior step. A saw blade is then guided along the distal 916 and side 918, 920 saw guiding surfaces to cut the base and sides of the intercondylar notch. The cut bone and intercondylar notch guide are then removed.

It will be understood by those skilled in the art that the foregoing has described illustrative embodiments of the present invention and that variations may be made to these embodiments without departing from the spirit and scope of the invention defined by the appended claims. For example the illustrative embodiments depict using saw guides and blades to make the bone cuts. However, the claimed methods and alignment guides could also be used with other bone removal systems to set their reference bases to achieve the desired position and rotation of prepared bone surfaces.

What is claimed is:

1. An extramedullary tibial cut guide assembly for cutting a proximal end of a tibia having a proximal end, a distal end, a tibial shaft, a tibial axis along the shaft, an anterior side parallel to a frontal plane, a medial side parallel to a sagittal plane, and a lateral side parallel to said sagittal plane, the tibial cut guide assembly comprising:

a support having a longitudinal support axis, the support axis positionable parallel to the sagittal plane when the support is mounted to a tibia;

a cross member mounted on the support, the cross member having a cross member axis perpendicular to the support axis, the cross member axis and support axis defining a guide plane that is positionable perpendicular to the sagittal plane when the support is mounted to the tibia, the cross member having a slope reference oriented at a predetermined slope angle relative to the guide plane;

a cut guide having a posterior face and an opposing anterior face, the cut guide comprising:

a cross member engaging end mounted on the cross member in engagement with the slope reference, such that the posterior face of the cut guide faces away from the longitudinal support axis to define a cutter path that is oriented obliquely to the guide plane, the cutter path also oriented obliquely to the sagittal plane when the support is mounted on the tibia whereby the cutter path defines one of an anterior-medial approach and an anterior-lateral approach to the tibia; and a cutter guide having a cut slot surface defining a cut plane, the cut slot surface extending between the posterior face and the anterior face, the cutter guide oriented at a predetermined slope angle relative to the guide plane as determined by the slope reference, such that the guide plane does not intersect the cut slot surface.

2. The tibial cut guide assembly of claim 1 further comprising a plurality of interchangeable cross members, each interchangeable cross member having a slope reference oriented at a different predetermined slope angle relative to the guide plane.

3. The tibial cut guide assembly of claim 1 wherein the cut guide is mounted on an arm projecting upwardly and inwardly from the cross member to position the cutter guide adjacent a tibia to be cut.

4. The tibial cut guide assembly of claim 1 wherein the cut guide is translatable along the cross member from a first position to a second position, the cutter guide defining parallel planes in the first and second position.

5. The tibial cut guide assembly of claim 4 wherein the cross member is translatable up and down along the support axis.

6. The tibial cut guide assembly of claim 1 further comprising a proximal adjustment mechanism actuable to change the spacing of a proximal end of the support and a proximal end of a tibia to change the angle of the support axis relative to a tibial axis.

7. The tibial cut guide assembly of claim 6 wherein the proximal adjustment mechanism comprises a screw threadingly engaging the support and abuttable with a proximal end of a tibia.

8. The tibial cut guide assembly of claim 1, wherein the posterior face of the cut guide is concave.

9. The tibial cut guide assembly of claim 1, wherein the cut guide further comprises a leg connecting the cross member engaging end and the cutter guide, the leg angling away from the guide plane to space the cutter guide from the cross member engaging end.

10. An extramedullary tibial cut guide assembly for cutting a proximal end of a tibia having a proximal end, a distal end, a tibial shaft, a tibial axis along the shaft, an anterior side parallel to a frontal plane, a medial side parallel to a sagittal plane, and a lateral side parallel to said sagittal plane, the tibial cut guide assembly comprising:

a support having a support axis, the support being mountable on said tibia with the support axis parallel to said tibial axis and spaced from said tibial axis;

a cross member mounted on the support, the cross member having a cross member axis which cooperates with the support axis to define a guide plane, the guide plane perpendicular to the sagittal plane when the support is mounted to the tibia, a cut guide comprising:
- an anterior face;
- an opposing posterior face; and
- a cut slot defining a cut slot surface extending between the anterior face and the posterior face and positioned to not intersect the guide plane, the cut guide being mounted on the support such that the posterior face of the cut guide faces away from the support axis to define a cutter path that is oriented obliquely to the guide plane, the cutter path also oriented obliquely to the sagittal plane when the support is mounted on the tibia, whereby the cut slot surface is oriented toward said tibia and between the anterior side and one of the medial and lateral sides of said tibia to cut the proximal end of said tibia when the support is mounted on said tibia.

11. The tibial cut guide assembly of claim 10 further comprising a cross member mounted on the support connecting the support and cut guide, the cross member having a cross member axis perpendicular to the support axis, the cross member axis and support axis defining a guide plane, the guide plane being positionable parallel to the frontal plane and the tibial axis, the cross member having a slope reference oriented at a predetermined slope angle relative to the guide plane.

12. The tibial cut guide assembly of claim 11 wherein the cut guide has a cross member engaging end and a cutter guide, the cross member engaging end being mounted on the cross member in engagement with the slope reference, the cutter guide defining a cut plane that is oriented at a predetermined slope angle relative to the guide plane as determined by the slope reference, the cutter guide being translatable along the cross member from a first position to a second position, the cutter guide defining parallel planes in the first and second position.

13. An extramedullary tibial cut guide assembly for minimally invasive resection of a tibia, the tibial cut guide assembly comprising:
- an alignment bar having a longitudinal alignment bar axis;
- a boom mounted on the alignment bar, the boom having a boom axis perpendicular to the alignment bar axis, the boom axis and alignment bar axis defining an anterior guide plane which does not intersect said tibia when the tibial cut guide assembly is mounted to the tibia, the boom having a slope reference oriented at a predetermined slope angle relative to the guide plane;

a cut guide comprising:
- a boom engaging end with a leg attached thereto, in which the boom engaging end is mounted on the boom in engagement with the boom slope reference and the leg angles away from the guide plane,
- a cutter guide mounted to the leg and spaced from the boom engaging end, the cutter guide having a guide surface defining a cut plane that is oriented at a predetermined slope angle relative to the guide plane as determined by the boom slope reference, whereby the guide surface of the cutter guide is oriented obliquely toward said tibia between the anterior side and one of the medial and lateral sides of said tibia to cut the proximal end of said tibia when the support is mounted on said tibia.

14. The tibial cut guide assembly of claim 13 wherein the cut guide slidingly engages the boom so that the cut guide can slide along the boom from a first position further from the alignment bar to a second position nearer to the alignment bar while maintaining the cut plane at a constant angle to the guide plane.

15. The tibial cut guide assembly of claim 14 wherein the boom is mounted for translation along the alignment bar axis so that moving the boom along the alignment bar axis changes the level of the cut plane.

16. The tibial cut guide assembly of claim 13 further including a depth gauge, the depth gauge including a blade having a reference end, the depth gauge being mounted on the assembly with the reference end a predetermined fixed distance from the cut plane as measured along the alignment bar axis.

17. The tibial cut guide assembly of claim 13 wherein the cutter guide comprises a saw blade slot defining a plane for a saw blade.

18. The tibial cut guide assembly of claim 13, wherein the boom engaging end comprises a base having a base axis, and the cut plane of the cutter guide is perpendicular to the base axis.

* * * * *